United States Patent [19]

Classon et al.

[11] Patent Number: 5,747,473
[45] Date of Patent: May 5, 1998

[54] L-NUCLEOSIDE ANALOGUES AND PHARMACEUTICAL COMPOSITIONS

[75] Inventors: Björn Olof Classon, Stockholm; Bengt Bertil Samuelsson, Onsala; Ingemar Sven-Anders Kvarnström, Linköping; Lars Göran Svansson; Stefan Carl Tore Svensson, both of Linköping, all of Sweden

[73] Assignee: Medivir AB, Huddinge, Sweden

[21] Appl. No.: 516,551

[22] Filed: Aug. 18, 1995

Related U.S. Application Data

[62] Division of Ser. No. 30,168, filed as PCT/SE91/00653 Oct. 2, 1990, Pat. No. 5,473,063.

[30] Foreign Application Priority Data

Oct. 2, 1990 [SE] Sweden ............... 9003151

[51] Int. Cl.$^6$ .............. C07H 19/10; C07H 19/20; A61K 31/70
[52] U.S. Cl. .............. 514/45; 514/46; 514/49; 514/50; 514/51; 514/81; 514/86; 536/26.23; 536/26.26; 536/26.7; 536/26.8; 536/27.6; 536/27.8; 536/27.81; 536/28.5; 536/28.51; 536/28.52; 536/28.53; 536/28.54; 536/28.55; 544/264; 544/265; 544/323; 544/322; 544/298; 544/309; 544/326; 544/242
[58] Field of Search ............... 536/27.6, 27.8, 536/27.81, 28.5, 28.51, 28.52, 28.53, 28.54, 28.55, 26.23, 26.26, 26.7, 26.74, 26.8; 514/45, 46, 47, 48, 49, 50, 51, 81, 86; 544/264, 265, 298, 309, 322, 323, 326

[56] References Cited

U.S. PATENT DOCUMENTS

| | | | |
|---|---|---|---|
| 3,116,282 | 12/1963 | Hunter | 536/27.4 |
| 3,817,982 | 6/1974 | Verheyden et al. | 536/27.14 |
| 4,247,544 | 1/1981 | Bergstrom et al. (II) | 514/49 |
| 4,267,171 | 5/1981 | Bergstrom et al. (I) | 514/49 |
| 4,724,232 | 2/1988 | Rideout et al. | 514/50 |
| 5,473,063 | 12/1995 | Classon et al. | 536/122 |

FOREIGN PATENT DOCUMENTS

| | | |
|---|---|---|
| 0286825 | 10/1988 | European Pat. Off. . |
| 0322384 | 6/1989 | European Pat. Off. . |
| 0357571 | 3/1990 | European Pat. Off. . |
| 0391411 | 10/1990 | European Pat. Off. . |
| 2040177 | 1/1971 | France . |
| 57-146798 | 9/1982 | Japan . |
| 3223264 | 1/1990 | Japan . |
| 8808001 | 10/1988 | WIPO . |

OTHER PUBLICATIONS

Acton et al., "Improved Antitumor Effects in 3'-Branched Homologs of 2'-Deoxythioguanosine. Synthesis and Evaluation of Thioguanine Nucleosides of 2,3-Dideoxy-3-(hydroxymethyl)-D-*erythro*-pentofuranose," *J. Medicinal Chem.*, 22(5), 518–525 (1979).

Shuto et al., "Chemical Conversion of Uridine to 3'-Branched Sugar Nucleosides (Nucleosides and Nucleotides. 42)," *Nucleosides & Nucleotides*, 1(3), 263–273 (1982).

Suemune et al., "Enzymatic Procedure for the Synthesis of Prostaglandin A$_z$," *Chem. Pharm. Bull.*, 36(1), 15–21 (1988).

Okabe et al., "Synthesis of Dideoxynucleosides ddC and CNT from Glutamic Acid, Ribonolactone, and Pyrimidine Bases," *J. Org. Chem.*, 53(20), 4780–4786 (1988).

Chong et al., "Facile Preparation of (2R,3S)–and (2S, 3R)–3–([[(4–Bromobenzyl)oxy]methyl] oxirane–2–methanol via Asymmetric Epoxidation," *J. Org. Chem.*, 52(12), 2596–2598 (1987).

Barr et al., "The Synthesis of Nucleosides Derived From 5–Ethynyluracil and 5–Ethynylcytosine," *J. Chem. Soc., Perkin Trans. I*, (10), 1263–1267 (1978).

Swierkowski et al., "A Nonmutagenic Thymidine Analog with Antiviral Activity. 5–Ethyldeoxyuridine," *J. Medicinal Chem.*, 12, 533–534 (May 1969).

*Primary Examiner*—John Kight
*Assistant Examiner*—L. Eric Crane
*Attorney, Agent, or Firm*—Birch, Stewart, Kolasch & Birch, LLP

[57] ABSTRACT

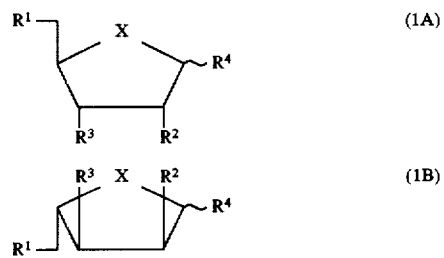

Novel antiviral compounds of formulae (1A) and (1B), wherein X and $R_1$–$R_4$ are as stated in claim 1 in the form of an α- or β-anomer or a mixture thereof, and pharmaceutically acceptable salts thereof, are disclosed, as well as a new method for preparation thereof. Said compounds can be used for treatment of infections caused by viruses requiring reverse transcriptase for replication, such as HIV and hepatitis B virus.

14 Claims, No Drawings

L-NUCLEOSIDE ANALOGUES AND PHARMACEUTICAL COMPOSITIONS

This application is a divisional of application Ser. No. 08/030,168, filed as PCT/SE91/00653 Oct. 2, 1990, now U.S. Pat. No. 5,473,063, the entire contents of which are hereby incorporated by reference.

FIELD OF THE INVENTION

The present invention relates to novel chemical compounds and pharmaceutically acceptable salts thereof which can be used in therapy for therapeutic and prophylactic treatment of the acquired immuno deficiency syndrome (AIDS) and infections caused by viruses requiring reverse transcriptase for replication, such as human immuno deficiency viruses and hepatitis B virus, and also for treatment of other virus diseases, such as those of herpes viruses, diseases which include both common infections and neoplastic diseases, i.e. cancer.

BACKGROUND OF THE INVENTION

The effects of viruses on bodily functions is the end result of changes occurring at the cellular and subcellular levels. The pathogenic changes at the cellular level are different for different combinations of viruses and host cells. While some viruses cause a general destruction (killing) of certain cells, other may transform cells into a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpes virus group. Other important viral diseases are influenza A and B which are caused by influenza A and B virus, respectively. Another important common viral disease is viral hepatitis and especially hepatitis B virus infections are widely spread. Effective and selective antiviral agents are needed for treatment of these diseases as well as for other diseases caused by viruses.

Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leukemias, sarcomas, breast carcinomas, Burkitt lymphomas, nasophopharyngal carcinomas and cervical cancers where RNA tumor viruses and herpes viruses are involved. This makes the search for selective inhibitors of tumorogenic viruses and their functions an important undertaking in the efforts to treat cancer.

In the late seventies a new disease was reported, which subsequently was referred to as Acquired Immuno Deficiency Syndrome (AIDS). It is now generally accepted that a retrovirus referred to as HIV (Human Immunodeficiency Virus), formerly known as Human T-cell Lymphotrophic Virus (HTLV-III) or Lymphadenopathy Associated Virus (LAV) plays an essential role in the etiology of AIDS. Different types of HIV have been found, such as HIV-1 and HIV-2 and more are likely to be isolated.

AIDS is characterized by a profound immunodeficiency due to low numbers of a subset of lymphocyte-T-helper cells, which are one target for HIV infection. The profound immunodeficiency in AIDS patients makes these patients highly susceptible to a variety of opportunistic infections of bacterial, fungal, protozoal or viral etiology. The etiological agents among viral opportunistic infections are often found in the herpes virus group, i.e. herpes simplex virus (HSV), Varicella Zoster virus (VZV), Epstein-Barr virus (EBV) and, especially, cytomegalovirus (CMV). Other retroviruses affecting humans are HTLV-I and II and examples of retroviruses affecting animals are feline leukemia virus and equine infectious anaemia virus. Human diseases such as multiple sclerosis, psoriasis, tropical spastic paresis and Kawasaki disease have also been reported to be associated with retrovirus infections.

Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrosis and liver tumours. In some cases the hepatitis infections also take a rapid and severe course as in fulminant B hepatitis with about 90% mortality. At present there is no known effective treatment against hepatitis B infections. The replication of hepatitis B virus is similar to that of retrovirus and it contains the same essential viral reverse transcriptase activity.

GENERAL OUTLINE OF THE INVENTION

A great number of nucleoside analogues exhibit several antimetabolic activities. They do so by substituting for or competing with the naturally occuring nucleosides. Recently some nucleoside analogues have been described, which inhibit in cell culture the multiplication of human immuno deficiency virus (HIV, also called HTLV-III, LAV) the causative agent of AIDS and AIDS-related complex (ARC). The nucleoside analogues described which inhibit HIV multiplication all have the β-D-furanosyl configuration.

We have now found that activities for inhibition of HIV multiplication are exhibited by nucleoside analogues in which the 2'-hydroxyl or 3'-hydroxyl is substituted for by a methyl or hydroxymethylene group or another methylene derivative thereof. The furanosyl moiety may have a D-configuration or L-configuration.

PRIOR ART

Some of the compounds and intermediates of the invention have been described previously.

J. Med. Chem. Vol 22, 1979, 518–525 describes the synthesis of methyl 2,3-dideoxy-3-C-(hydroxymethyl)-β-D-erythropentofuranoside as well as the corresponding dibenzyl- and dibenzoyl derivative. The chloro derivative 5-0-benzoyl-3-C-[(benzoyloxy)methyl)]-2,3-dideoxy-D-erythro-pentafuranosyl chloride was coupled with 2-acetamido-6-chloropurine. The product was processed further to give the two anomers of 2-amino-9-[2,3-dideoxy-3-C-3-(hydroxymethyl)-D-erythro-pentofuranosyl]-9H-purine-6(1H)-thione which were tested for antitumor activity. The synthesis of 2,3'-dideoxy-3'(R)-hydroxymethyl uridine has been described in Nucleosides & Nucleotides 1 (1982) 263–273. Uridine was converted to 1-(3-amino-2,3-dideoxy-β-D-glucopyranosyl)uracil via a multistage sequence, which was further reacted via ring contraction, epimerization and reduction to give 2',3'-dideoxy-3'(R)-hydroxymethyl uridine.

α-Anomer compounds of the formula

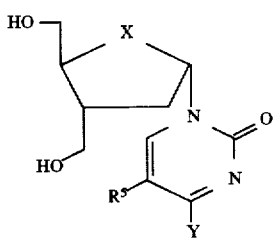

wherein X is O, S or CH$_2$; Y is OH or NH$_2$ and R$^5$ is H, CH$_3$, CH$_2$CH$_3$, CH$_2$CH$_2$CH$_3$, CH(CH$_3$)$_2$, CH=CH$_2$, C≡CH or CH=CH—CH$_3$, and their β-anomers are described in the International Patent Application No. PCT/SE88/00169, (publication No. WO 88/08001).

DISCLOSURE OF THE INVENTION

The present invention relates to new compounds of the formula 1A OR 1B

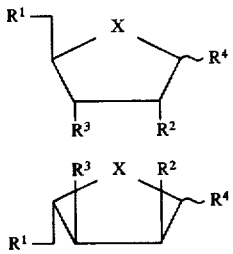

wherein X is O, S, SO, SO$_2$ or CH$_2$; R$^1$ is OH, OPO(OH)$_2$, OPO(OH)—O—PO(OH)$_2$, OPO(OH)—O—PO(OH)—O—PO(OH)$_2$ or (CH$_2$)$_n$OCH$_2$ PO(OH)$_2$ wherein $n$ is O—2; R$^2$ is H and R$^3$ is CH$_3$, CH$_2$OH, CH$_2$OCH$_3$, CH$_2$SH, CH$_2$F or CH$_2$N$_3$; or R3 is H and R$^2$ is CH$_3$, CH$_2$OH, CH$_2$OCH$_3$, CH$_2$SH, CH$_2$F or CH$_2$N$_3$;

R$^4$ is

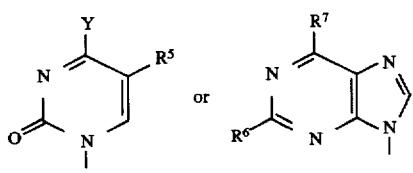

wherein Y is OH, NH$_2$ and R$^5$ is CH=CH$_2$, C≡CH, CH=CH—CH$_3$, —C≡CH$_3$ thien-2-yl, thien-3-yl, H, CH$_3$, C$_2$H$_5$, n—C$_3$H$_7$ or i—C$_3$H$_7$;

R6 and R7 are the same or different and are H, F, Cl, OH, NH$_2$ or SH;

and pharmaceutically acceptable salts thereof.

In formula 1A the sugar has either the α-D- or the β-D-configuration.

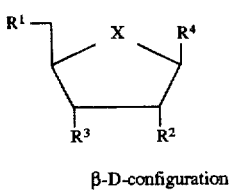

β-D-configuration

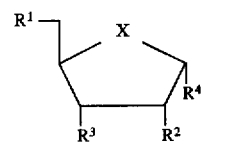

α-D-configuration

In formula 1B the sugar has either the α-L- or the β-L-configuration.

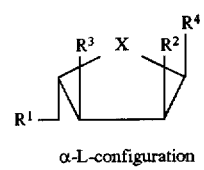

α-L-configuration

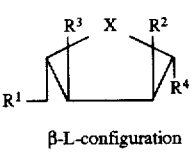

β-L-configuration

Said compounds have been found to inhibit the multiplication of human immunodeficiency virus (HIV).

The invention consequently also refers to the compounds of the formulas 1A and 1B for use in therapy. The compounds of the formulas 1A and 1B are useful as therapeutic and/or prophylactic agents in the control and treatment of HIV virus infections in man. In a more general aspect, the compounds of the formulas 1A and 1B are useful as therapeutic and/or prophylactic agents in the control and treatment of infections caused by retroviruses and hepatitis B virus in mammals and man.

All retroviruses, including HIV, require the enzyme reverse transcriptase for replication.

Hepatitis B virus (HBV) is a DNA virus with a unique circular double-stranded DNA genome which is partly single-stranded. It contains a specific DNA polymerase required for viral replication. This DNA polymerase also acts as a reverse transcriptase during the replication of HBV DNA via an RNA intermediate.

Other possible uses of the compounds of formulas 1A and 1B are as antimetabolic and antineoplastic compounds and compounds for treatment of other viruses.

One possible use for the compounds of the formulas 1A and 1B is in the treatment of herpes virus infection. Among the herpes viruses may be mentioned herpes simplex type 1 and 2, varicella (herpes zoster), virus causing infectious mononucleosis (i.e. Epstein-Barr virus), cytomegalovirus and human herpes virus type 6. Important diseases caused by herpes viruses are herpes dermatitis (including herpes labialis), herpes genitalis, herpes keratitis, herpes encephalitis and herpes zoster.

Another possible area of use for the compounds of the present invention is in the treatment of cancer and tumors, particularly those caused by viruses. This effect may be obtained in different ways, i.e. by inhibiting the spread of viruses from transformed cells to other normal cells and by arresting the growth of virus-transformed cells.

Another possible area of use for the compounds of the present invention is in the treatment of parasitic infections. Parasites usually have a specific enzyme activities for nucleoside metabolism making them amenable for therapy by nucleoside analogs. Among the parasites may be mentioned the Schistosama, the Dipetalonema, the Trypanosoma, the Leishmania, the Trichononas Emereia, the Plasmodium and the Toxoplasma families. In this regard, an important member of the Protozoa is Pneumocystis carinii, causing severe opportunistic infection in AIDS patients.

The invention furthermore provides:

A pharmaceutical composition comprising a compound of the formulas 1A and 1B as an active ingredient and a pharmaceutically acceptable carrier, including liposomes; and A method for therapeutic and/or prophylactic treatment of virus infections in an animal or human host in need of treatment comprising administering an effective amount of a compound of the formulas 1A and 1B.

It is a preferred aspect of the invention to treat infections caused by viruses requiring reverse transcriptase for replication, including human immuno deficiency viruses and hepatitis B virus.

The invention also relates to the use of a compound of the formulas 1A and 1B for the manufacture of a medicament for therapeutic and/or prophylactic treatment of the acquired immuno deficiency syndrome and infections caused by viruses requiring reverse transcriptase for replication.

Preferably they can be used for the treatment of infections caused by HIV viruses or hepatitis B virus.

The following compounds of formulas 1A are particularly useful in medical therapy.

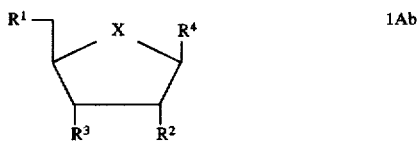

wherein X is O, S and $CH_2$; $R^1$ is OH; $R^2$ is H and $R^3$ is $CH_2OH$; $R^3$ is H and $R^2$ is $CH_2OH$;

$R^4$ is

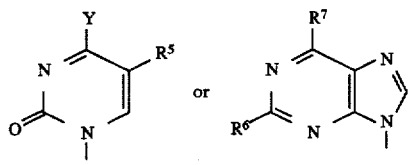

Y is $NH_2$ and $R^5$ is H; Y is OH and $R^5$ is H, $CH_3$, C≡CH, CH=CH—$CH_3$; $R^6$ is $NH_2$ and $R^7$ is H, OH, SH or $NH_2$; $R^6$ is H and $R^7$ is OH, SH or $NH_2$; $R^6$ is F or Cl and $R^7$ is OH, SH or $NH_2$; $R^6$ is OH and $R^7$ is OH.

Examples of pharmaceutically acceptable salts of the compounds of formulas 1A and 1B include base salts, e.g. derived from an appropriate base, such as alkali metal (e.g. sodium, potassium, alkaline earth metal, e.g. magnesium) salts, ammonium and tetraalkylammonium. Physiologically acceptable acid salts include salts of organic carboxylic acids such as acetic, lactic, gluconic, citric, tartaric, maleic, malic, pantothenic, isethionic, oxalic, lactobionic and succinic acids; organic sulfonic acids such as methanesulfonic, ethanesulfonic, benzenesulfonic, p-chlorobenzenesulfonic and p- toluenesulfonic acids and inorganic acids such as hydrochloric, hydroiodic, sulfuric, phosphoric and sulfamic acids.

Mono-, di- and triphosphate esters of the compounds are also included in the invention. Physiologically acceptable counterions of the phosphate groups include inorganic and organic counterions. Inorganic counterions are for example ammonium, sodium, potassium, lithium, magnesium and calcium. Organic counterions are derived from non-toxic bases, such as primary, secondary and tertiary amines, including naturally occuring amines. Examples of such amines are diethylamine, triethylamine, isopropylamine, ethanolamine, morpholine, 2-diethylaminoethanol, glucosamine, N-methylglucamine, piperazine and dicyclohexylamine.

In clinical practice the nucleoside analogues of the formula I will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragées, capsules, granulates, suspensions, elixirs, syrups, solutions, liposomes etc. Usually the active substance will comprise between 0.05 and 20% for preparations intended for injection and between 10 and 90% for preparations intended for oral administration.

In the treatment of patients suffering from retrovirus, especially HIV, or hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of the patient etc., and may have to be individually adjusted. As a possible range for the amount of the compounds of the invention or a physiologically acceptable salt thereof to be administered per day may be mentioned from about 10 mg to about 10000 mg, preferentially 50–500 mg for intravenous administration and preferentially 50–3000 mg for oral administration.

Compounds of the formulas 1A and 1B can cooperate synergistically or additively with a wide range of other therapeutic agents, thereby enhancing the therapeutic potential of both agents without adding the toxic effects, thus increasing the therapeutic ratio.

Therefore, a compound of formulas 1A and 1B or a pharmaceutically acceptable derivative thereof can be used in combination therapy, wherein the two active agents are present in a ratio resulting in an optimal therapeutic ratio. This can be provided either by a synergistic effect against the viral infection and/or by a decrease in toxicity while maintaining a therapeutic effect which is additive or synergistic.

The optimal therapeutic ratio is observed when the two agents are present in a ratio of 500:1 to 1:500, preferably 100:1 to 1:100, particularly 20:1 to 1:20 and especially 10:1 to 1:10.

Said combination may conveniently be administered together, for example, in a unitary pharmaceutical formulation, or separately for example as a combination of tablets and injections administered at the same time or at different times, in order to achieve the required therapeutic effect.

The compounds of the formulas 1A and 1B are potentiated by interferons, other antiviral agents such as foscarnet, AZT, fluorothymidine, dideoxyinosine, dideoxydidehydrothymidine, 9-|4-hydroxy-(2-hydroxymethyl)butyl|guanine, acyclovir, HIV protease inhibitors, immunomodulators, interferon inducers and growth factors.

Particularly preferred types of interferon are a, b and c interferon inducers.

Other combinations suitable for use according to the present invention include those wherein the second agent is, for example, interleukin II, foscarnet esters, inhibitors of HIV protease such as pepstatin, steroids, medications such as levamisol or thymosin to increase lymphocyte numbers and/or function as appropriate, or G-CSF and other factors regulating cell functions.

METHOD OF PREPARATION

The compounds of the invention may be prepared as outlined below, however, the invention is not limited to these methods. The compounds may also be prepared by processes described in the known art.

The synthesis of 1A where $R^1$ is OH, $R^2$ is H, $R^3$ is $CH_2OH$ and $R^4$ is uracil-1-yl has been previously described in Nucleosides and Nucleotides, vol 1, 1982, 263–273. This derivative, suitably protected can be converted to other nucleoside derivatives by processes known in the art such as transglycosylation with suitably derivatized purine or pyrimidine bases or by chemical transformations of uracil.

The synthesis of methyl 2,3-dideoxy-3-C-(hydroxymethyl)-β-D-erythropentafuranoside and methyl 5-O-benzoyl-3-C-[(benzoyloxy)methyl]-2,3-dideoxy-β-D-erythro-pentofuranoside, starting from D-glucose, is described in J. Med. Chem., vol. 22, 1979, 518–525.

This latter compound was converted to 5-O-benzoyl-3-C-[(benzoyloxy)methyl]-2,3-dideoxy-D-erythropentofuranosyl chloride which was glycosylated with silylated 2-acetamido-6-chloropurine. The carbohydrate part of 1A can also be prepared from a protected 2,3-dideoxy-D-glycero-pent-2-enono-1,4-lactone through a 1,4-Michael type addition with an appropriate carbon nucleophile in an analogous manner as described in Carbohydr. Res. Vol. 183, 1988, 261–275 and J. Org. Chem., Vol. 53, 1988, 4780–4786.

A compound of the formula

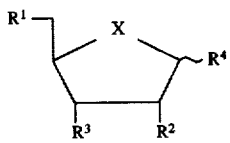

1A wherein X, $R^1$, $R^2$, $R^3$ and $R^4$ are as defined in claim 1 can be prepared by condensing a glycoside as comprised in the formula to the N-1 position of a pyrimidine derivative or to the N-9 position of a purine derivative.

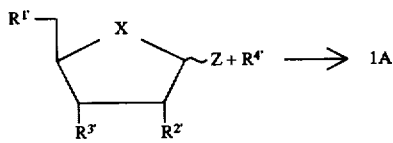

wherein Z is Cl, Br, J, acyloxy or alkoxy, and $R^{1'}$ $R^{2'}$ and $R^{3'}$ are $R^1$, $R^2$ and $R^3$ respectively, as defined above or with the proviso that when $R^1$ or $R^2$ is OH then 0 must have a protecting group, $R^{4'}$ is $R^4$ as defined above, having a silyl, acyl or alky-protecting group A compound of the formula

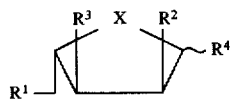

1B wherein X, R, $R^2$ and $R^3$ are as defined in claim 1, can in the same way be prepared by condensing a glycoside as comprised in the formula to the N-1 position of a pyrimidine derivative or to the N-9 position of a purine derivative

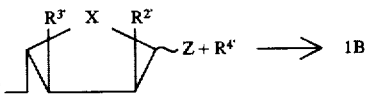

wherein Z is Cl, Br, J, acyloxy or alkyloxy and $R^{1'}$, $R^{2'}$ and $R^{3'}$ are R, $R^2$ and $R^3$ respectively as defined above or with the proviso that when $R^1$ or $R^2$ is OH must have a protecting group, $R^{4'}$ is $R^4$ as defined above, having a silyl, acyl or alkyl protecting group.

According to a new method the compounds of the formula

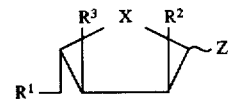

wherein X, $R^1$, $R^2$ and $R^3$ are as defined in claim 1 and Z is Cl, Br, J, aceloxy or alkoxy, can be prepared by reacting a protected butan-1,4-diol-2,3 epoxide with a nucleophile containing 3 or 4 carbon atoms with a double bond, followed by transforming the double bond and ring closure.

Compounds of the type 1A can thus be synthesized as outlined below in Scheme 1 or as in Scheme 2–4.

Scheme 1

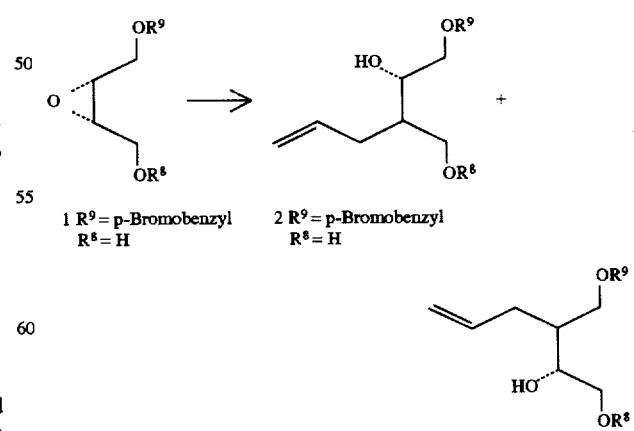

1 $R^9$ = p-Bromobenzyl
$R^8$ = H

2 $R^9$ = p-Bromobenzyl
$R^8$ = H

3

-continued
Scheme 1

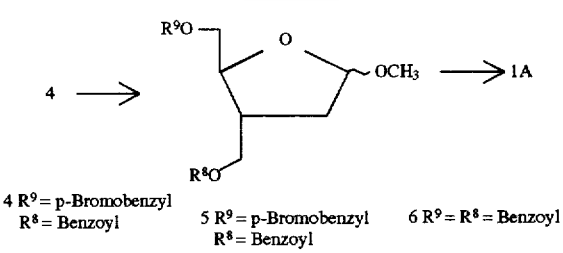

4 R⁹ = p-Bromobenzyl
R⁸ = Benzoyl

5 R⁹ = p-Bromobenzyl
R⁸ = Benzoyl

6 R⁹ = R⁸ = Benzoyl

This method is particularly useful, since by employing an epoxide with the chirality enantiomeric to that of 1, the L-sugars of the formula 1B are also synthesized. When $R^8$ is H, compounds with the different functionalities of $R^3$ are selectively prepared.

By analogous procedures the compounds wherein X is S are prepared. S may then be oxidized to SO and $SO_2$.

Compounds wherein X is $CH_2$ can be prepared as follows

Scheme 2

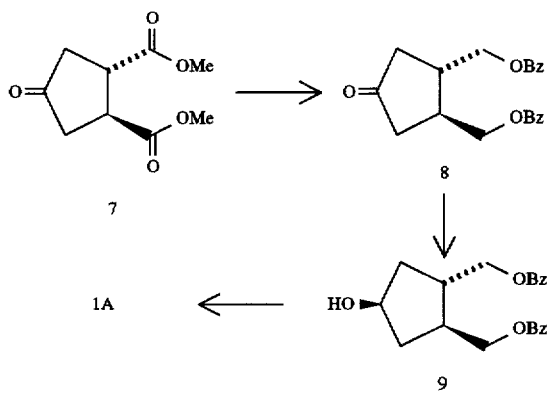

The chiral epoxide 1 [(2S,3R)-3-[[((4-bromobenzyl)oxy] -methyl]oxirane-2-methanol] where $R^9$ is p-bromobenzyl and $R^8$ is hydrogen can be prepared as described in J. Org. Chem. Vol. 52, 1987, 2596–2598. $R^9$ and/or $R^8$ may be any base stable protecting group such as benzyl or alkyl or a silyl protecting groups. Epoxide 1 can be treated with allyl magnesium bromide or an allyl anion equivalent to give a mixture of 2 and 3 which are separated by conventional techniques such as chromatography or crystallization. In the case where $R^8$ is hydrogen the free hydroxyl in 2 is at this stage preferably protected with an acyl group, preferably benzoyl. Oxidative cleavage of the double bond and treatment of the product with anhydrous methanol containing a catalytic amount of acid gives 4.

Compound 4 may be coupled to silylated purines or pyrimidines using acid catalysis to give the nucleoside derivative as an α- and β-mixture. In 4, when $R^9$ and $R^8$ are not both benzoyl, 4 is preferably converted to this derivative by conventional deblocking and blocking procedures. The α- and β-anomeric mixture of nucleosides is preferably deprotected after which the α- and β-anomers are separated by conventional techniques such as chromatography or crystallization, to give 1A as defined earlier in which $R^1$ and $R^3$ are hydroxyl and hydroxymethyl respectively.

Compounds of the type 1B are prepared entirely analogously by starting with an epoxide corresponding to 1 but having the opposite chirality.

Compounds wherein X is $CH_2$ are prepared from 7 (Chem. Pharm. Bull. 1988, 36, 15) by protecting the ketone as a ketal and reducing the esters to ethers using lithium aluminium hydride and hydrolyzing the ketal to give 8. Reduction of the keton gave 9 which was condensed with a suitable purine derivative. Deprotection gave 1A. Compounds of the type 1B where X is $CH_2$ were synthesized in the same way.

Compounds of the type 1A wherein X is O and $R^2$ is $CH_2OH$, $CH_2F$ or $CH_2N_3$ are prepared from (S)-4-( tert.-butyldiphenylsilyloxy)methyl-γ-butyrolactone(11) by acylation with ethyl formate and reduction with sodium borohydride and acylation to give 12 after separation using silica gel column chromatography. Reduction with dialkylaluminium hydride followed by acylation gave 13. This compound was glycosylated with suitable nucleoside base derivatives.

Scheme 3

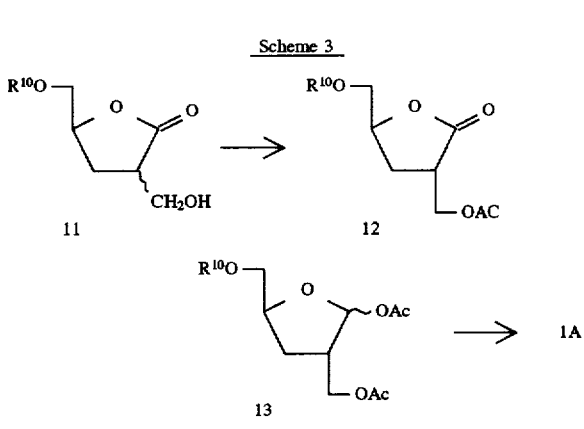

$R^{10}$ = tert.-butyl-diphenyl-silylchloride

Scheme 4

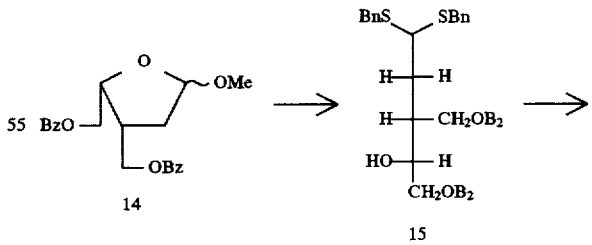

-continued
Scheme 4

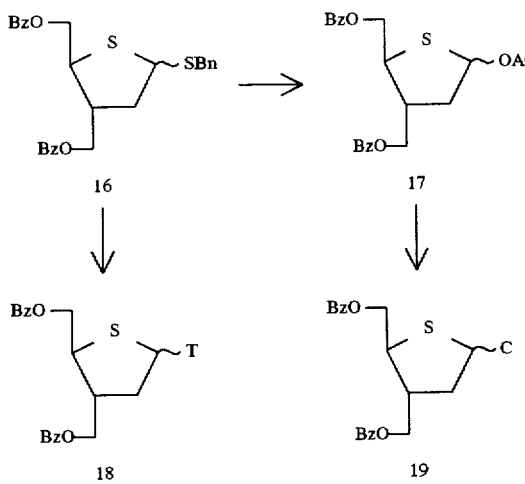

Bz = benzoyl  Bn = benzyl  T = thymidine  C = cytosine

Compounds of the type 1A wherein X=S are prepared from 14 by treatment with benzyl mercaptane and stannic chloride to give 15. Ring closure of 15 using triphenylphosphine and triiodoimidazole afforded 16. A portion of compound 16 was condensed with silylated thymine. The rest of compound 16 was treated with mercuric acetate to give 17 which was condensed with silylated cytosine.

The following illustrates the principle and the adaption of the invention, however, without being limited thereof. Temperature is given in degrees Celsius. Concentrations were performed under diminished pressure (1–2 kPa) at a bath temperature not exceeding 40° C. NMR spectra were measured with a JEOL GX-270 or FX-100 instrument, using $D_2O$ or $CDCl_3$ solutions. TMS (for $CDCl_3$) and TSP or dioxane (for $D_2O$) were used as internal standards. The shifts are reported in ppm. UV absorption spectra were recorded with a Perkin-Elmer Lamda 5 spectrophotometer. TLC were performed on Merck precoated 60 F-254 plates. Spots were visualized by UV light and/or charring with 8% sulfuric acid. Column chromatography was performed using silica gel 60 (0.040–0.063 MM, Merck). HPLC was performed on a prepacked steel column (250×25 mm) using Polygosil 60-7, C-18 (Macherey-Nagel). Organic phases were dried over anhydrous magnesium sulphate. Optical rotations were determined with a Perkin-Elmer 141 polarimeter.

This invention can be illustrated by the following examples:

Example 1

1-[2',3'-Dideoxy-3'-C-(hydroxymethyl)-β-D-erythro-pentofuranosyl]-cytosine.

A suspension of cytosine (120 mg, 1.08 mmol) and a small chrystal of $(NH_4)_2SO_4$ in hexamethyldisilazane (2 ml) and trimethylchlorosilane (0.2 ml) was refluxed until a clear solution was obtained. The solution was concentrated in vacuo and co-evaporated with dry xylene. The solid residue was dissolved in dry $CH_2Cl_2$ (2 ml) under nitrogen and methyl-5-0-benzoyl-3-[(benzoyloxy)methyl]-2,3-dideoxy-D-erythro-pentofuraoside (170 mg, 0.46 mmol) was added followed by the addition of a t-butyl-dimethylsilyl-triflate (0.22 ml, 0.96 mmol). After 24 h at room temperature the reaction was quenched by the addition of aqueous $NaHCO_3$ (sat.) and the resulting mixture was stirred for 30 minutes. The solution was diluted with $CH_2Cl_2$ and washed with $NaHCO_3$ (sat.), dried, filtered and concentrated to give an anomeric mixture of the protected nucleoside. This mixture was treated with methanolic ammonia (20 ml, sat.) for 24 h at room temperture. After concentration, the residue was dissolved in water and extracted with $CH_2Cl_2$. The aqueous phase was concentrated to a small volume and was applied to a semi-preparative C-18 reversed phase chromatography column and eluted with water containing 2% methanol. First the α-isomer was collected, followed by the β-isomer. The appropriate fractions were combined and evaporated to give 33 mg of the α-anomer (30%) and 27 mg of the β-anomer (24%). α-Anomer: $[\alpha]^{26}D$: −54° (c 0.3, $H_2O$); UV ($H_2O$) $\lambda_{max}$: 272 nm (ε10894); $^1$H-NMR (270 MHz, $D_2O$): 1.92 (m, $J_{2'a,2'b}$=13.5 Hz, $J_{2'a,3}$=9 Hz, $J_{2'a,1}$=6.5 Hz, 1H, H-2'a); 2.5 (m, 1H, H-3'); 2.7 (m, $J_{2'a,2'b}$=13.5 Hz, $J_{2'a,3}$=8H2, $J_{2'a,1}$=6 Hz, 1H H-2'b); 3.67, 3.69 (d and q, overlapping, $J_{6',3}$=6.2 Hz, $J_{5'a,5'b}$=12.5 Hz, $J_{4',5'a}$=5.3 Hz, 3H, H-6' and H-5'a); 3.85 (q, $J_{5'a,5'b}$=12.5 Hz, $J_{4',5'b}$=3 Hz, 1H, H-5'b); 4.28 (m, $J_{3',4}$=8 Hz, $J_{4',5'a}$=5.3 Hz, $J_{4',5'b}$=3 Hz, 1H, H-4'); 6.1 (d and q, overlapping, $J_{5,6}$=7.3 Hz, $J_{1,2}$=6.5 Hz, 2H,H-5 and H-1'); 7.8 (d, $J_{5,6}$=7.3 Hz, 1H, H-6); $^{13}$c-NMR (25.05 MHz, $D_2O$): 36.4 (C-2'); 42.3 (C-3'); 62.7, 63.6 (C-5', C-6'); 84.4, 88.2 (C-1', C-4'); 96.6 (C-5); 141.9 (C-6); 158.1 (C-2); 166.8 (C-4). β-Anomer: $[\alpha]^{26}{}_D$: +64° (c 0.27, $H_2O$); UV ($H_2O$) λ max: 272 nm (δ 9208); $^1$H-NMR (270 MHz, $D_2O$): 2.2–2.46 (m, 3H, H-2; H-3'); 3.68 (d, $J_{3',6}$=5.5 Hz, 2H, H-6'); 3.76 (dd, $J_{4',5'a}$=5.5 Hz, $J_{5'a,5'b}$=12.5 Hz, 1H, H-5'a); 3.92 (dd, $J_{4',5'b}$=2.9 Hz, $J_{5'a,5'b}$=12.5 Hz, 1H, H-5'b); 4.01 (m, $J_{3',4}$=8.1 Hz, $J_{5a',4}$=5.5 Hz, $J_{5'b,4}$=2.9 Hz, 1H, H-4'); 6.05 (3, $J_{5,6}$=7.3 Hz, 1H, H-5); 6.11 (dd, $J_{1',2'a}$=7.0 Hz, $J_{1',2'b}$=4.0 Hz, 1H, H-1'); 7.91 (d, $J_{5,6}$=7.3 Hz, 1H, H-6); $^{13}$C-NMR (25.05 MHz, $D_2O$): 36.1 (C-2'); 40.8 (C-3'); 62.7, 63.1 (C-5', C-6'); 84.7, 87.1 (C-1', C-4'); 96.5 (C-5); 142.2 (C-6); 158.2 (C-2); 166.8 (C-4).

Example 2

9-[2',3'-Dideoxy-3'-C-(hydroxymethyl)-β-D-erythro-pentofuranosyl]-adenosine; and

Example 3

9-[2',3'-Dideoxy-3'-C-(hydroxymethyl)-α-D-erythro-pentofuranosyl]-adenosine.

6-chloro-purine (200 mg, 1.3 mmol) was condensed with methyl 5-0-benzoyl-3-[(benzoyloxy)methyl]-2,3- dideoxy-D-erythro-pentofuranoside (280 mg, 0.76 mmol) following the same procedure as described in examples 1 and 2 but using acetonitrile was used instead of $CH_2Cl_2$ as solvent to give an anomeric mixture which after isolation was dissolved in methanolic ammonia (5 ml) and heated at 100 in a sealed tube. After 20 h the solvent was removed and the residue dissolved in water and extracted with $CH_2Cl_2$. The aqueous layer was concentrated to a small volume and was applied to a semi-preparative C-18 reversed phase chromatography column and eluted with water containing 8% methanol. First the α-isomer was eluted, followed by the β-isomer. The appropriate fractions were combined and evaporated to give 20 mg of the α-anomer (Example 3) (10%) and 40 mg of the β-anomer (Example 2) (20%).

α-isomer: $[a]^{26}{}_D$: +41° (c 0.23, $H_2O$); UV ($H_2O$) $\lambda_{max}$: 260 nm (e 12864); $^1$H-NMR (270 MHz, $D_2O$): 2.45 (m, 1H, H-2'a); 2.6 (m, 1H, H-3') 2.82 (m, $J_{2'b,1}$=6 Hz, $J_{2'b,3}$=7.8 Hz, $J_{2'b,2'a}$=14 Hz, 1H, H-2'b); 3.72 and 3.74 (q and d, overlapping, $J_{5'b,4}$=5.5 Hz, $J_{5'b,5'a}$=12.5 Hz, $J_{6',3}$=5.9 Hz, 3H, H-5'b and H-6'); 3.86 (q, $J_{5'a,4}$=2.9 Hz, $J_{5'a,5'b}$=12.5 Hz, 1H, H-5'a); 4.31 (m, 1H, H-4'); 6.35 (m, 1H, H-1'); 8.19 (s, 1H, H-2); 8.32 (s, 1H, H-8); $^{13}$C-NMR (25.05 MHz, D$_2$O): 35.5 (C-2'); 42.3 (C-3'); 62.5, 63.3 (C-5', C-6'); 83.8, 85.3 (C-1', C-4'); 119.4 (C-5); 140.3 (C-8); 148.9 (C-4); 153.0 (C-2); 155.9 (C-6).

β-isomer: [α]26$_D$: −17 (c 0.27, H$_2$O); UV (H$_2$O) λ$_{max}$: 260 nm (ε 10744); $^1$H-NMR (270 MHz, D$_2$O) 2.5 (m, 1H, H-3'); 2.67 (m, 2H, H-2'); 3.69 (q, J$_{5'a,4}$=5.1 Hz, J$_{5'a,5'b}$=12.5 Hz, 1H, H-5'a); 3.77 (d, J$_{6',3}$=5.5 Hz, 2H, H-6'); 3.87 (q, J$_{5'b,4}$=2.9 Hz, J$_{5'b,5'a}$=12.5 Hz, 1H, H-5'b); 4.13 (m, 1H, H-4'); 6.34 (m, 1H, H-1'); 8.18 (s, 1H, H-2); 8.32 (s, 1H, H-8). $^{13}$C-NMR (25.05, MHz D$_2$O); 35.7 (C-2'); 41.4 (C-3'); 62.8, 63.4 (C-5',C-6'); 85.0, 85.3 (C-1', C-4'); 119.2 (C-5); 140.5 (C-8); 148.7 (C-4); 153.0 (C-2); 155.8 (C-6).

Example 4

1-[2',3'-Dideoxy-3'-C-(hydroxymethyl)-β-D-erythro-pentofuranosyl]-thymine.

Thymine (150 mg, 1.19 mmol) was condensed with methyl 3-C-[(benzoyloxy)methyl]-5-O-p-bromobenzyl-2,3-dideoxy-D-erythro-pentofuranoside (205 mg, 0.47 mmol) following the same procedure as described in Examples 1 and 2 to give an anomeric mixture of the protected nucleoside. The mixture was dissolved in ethanol containing NaHCO$_3$ (excess) and was hydrogenated over Pd (10% on carbon, 1 atm) for 3 hours. After workup the residue was further reacted with methanolic ammonia for 24 h. After concentration the residue was dissolved in water and extracted with CH$_2$Cl$_2$. The aqueous layer was concentrated to a small volume and was subjected to semi-preparative C-18 reversed phase column chromatography and eluted with water containing 10% methanol. First the α-isomer was eluted, followed by the β-isomer. The appropriate fractions were combined and evaporated to give 40 mg of the α-anomer (33%) and 41 mg of β-anomer (33%).

α-Isomer: [α]$^{26}$$_D$: −3.6 (c 0.36, H$_2$O); UV (H$_2$O) λ$_{max}$: 268 nm (ε 13756); $^1$H-NMR (270 MHz, D$_2$O): 1.89 (d, J=1.1 Hz, 3H, 5-CH$_3$); 1.96 (m, J$_{2'a,2'b}$=13.2 Hz, J$_{2'a,3}$=9.9 Hz, J$_{2'a,1}$=7.7 Hz, 1H, H-2'a); 2.47 (m, 1H, H-3'); 2.6 (m, J2'a,2'b'=13.2 Hz, J$_{2'b,3}$=8.1 Hz, J$_{2'b,1}$=6.2 Hz, 1H, H-2'b); 3.64 and 3.68 (d and q overlapping, J$_{5'a,4}$=5.5 Hz, J$_{5'a,5'b}$=12.1 Hz, J$_{6',3}$=6.1 Hz, 3H, H-5'a, H-6'); 3.81 (q, J$_{5'b,4}$=2.9 Hz, J$_{5'b,5'a}$=12.1 Hz, H-5'b); 4.24 (m, J$_{3',4}$=8.4 Hz, J$_{4',5'a}$=5.5 Hz, J$_{4',5'b}$=2.9 Hz, 1H, H-4); 6.11 (q, J$_{1',2'a}$=7.7 Hz, J$_{1',2'b}$=6.2 Hz, 1H, H-1'); 7.59 (d, J=1.1 Hz, 1H, H-6); $^{13}$C-NMR (25.05 MHz, D$_2$O): 12.5 (5-CH$_3$); 35.7 (C-2'); 42.7 (C-3'); 62.6, 63.5 (C-5', C-6'); 84.2, 87.3 (C-1', C-4'); 111.6 (C-5); 138.1 (C-6); 152.4 (C-2); 167.3 (C-4).

β-Isomer: [α]$^{26}$$_D$: +17.8 (c 0.41, H$_2$O); UV (H$_2$O) λ$_{max}$: 268 nm (ε 8516); $^1$H-NMR (270 MHz, D$_2$O); 1.91 (s, 3H, 5-CH$_3$); 2.3 (m, 2H, H-2'); 2.5 (m, 1H, H-3'); 3.69 (d, J$_{3',6}$=5.9 Hz, 2H, H-6'); 3.76 (q, J$_{5'b,5'a}$=12.4 Hz, J$_{5'b,4}$=5.1 Hz, 1H, H-5'b); 3.9 (q, J$_{5'a,5'b}$=12.4 Hz, J$_{5'a,4}$=2.9 Hz, 1H, H-5'a); 3.99 (m, J$_{4',5'a}$=2.9 Hz, J$_{4',5'b}$=5.1 Hz, J$_{4',3}$=8.1 Hz, 1H, H-4$^1$); 6.14 (q, J$_{1',2'a}$=4.8 Hz, J$_{1',2'b}$=6.6 Hz, 1H, H-1'); 7.73 (d, J=1.1 Hz, 1H, H-6). $^{13}$C-NMR (25.05 MHz, D$_2$O): 12.5 (5-CH$_3$); 35.4 (C-2'); 40.9 (C-3'); 62.8, 62.9 (C-5', C-6'); 84.5, 86.1 (C-1', C-4'); 111.7 (C-5); 138.3 (C-6); 152.7 (C-2); 167.5 (C-4).

Analogously the corresponding nucleoside analogs of the formula 1B, having the L-configuration, were synthesized in examples 5–10. The synthetic strategy was identical to that one outlined in scheme 1 and described in the detail for the preparation of Examples 1–4 and their starting materials. For Examples 5–10, the starting material corresponding to formula 1 of scheme 1 was:

(2R,3S)-3-[[(4-bromobenzyl)oxy]methyl]oxirane-2-methanol.

Example 5

1-[2',3'-Dideoxy-3'-C-(hydroxymethyl)-β-L-erythro-pentofuranosyl]-cytosine; and

Example 6

1-[2',3'-Dideoxy-3'-C-(hydroxymethyl)-α-L-erythro-pentofuranosyl]-cytosine.

The α-anomer had [α]$_D$$^{22}$: +57.3° (c 0.61, H$_2$O); UV (H$_2$O) λ$_{max}$: 273 nm (ε 7647); $^1$H-NMR (270 MHz, D$_2$O): 1.92 (m, J$_{2'a,2'b}$=13.5 Hz, J$_{2'a,3}$=9 Hz, J$_{2'a,1}$=6.5 Hz, 1H, H-2'a); 2.5 (m, 1H, H-3'); 2.7 (m, J$_{2'a,2'b}$=13.5 Hz, J$_{2'a,3}$=8H2, J$_{2'a,1}$=6 Hz, 1H H-2'b); 3.67, 3.69 (d and dd, overlapping, J$_{6',3}$=6.2 Hz, J$_{5'a,5'b}$=12.5 Hz, J$_{4',5'a}$=5.3 Hz, 3H, H-6' and H-5'a); 3.85 (dd, J$_{5'a,5'b}$=12.5 Hz, J$_{4',5'b}$=3 Hz, 1H, H-5'b); 4.28 (m, J$_{3',4}$=8 Hz, J$_{4',5'a}$=5.3 Hz, J$_{4',5'b}$=3 Hz, 1H, H-4'); 6.1 (d and t, overlapping, J$_{5,6}$=7.3 Hz, J$_{,2}$=6.5 Hz, 2H, H-5 and H-1'); 7.8 (d, J$_{5,6}$=7.3 Hz, 1H, H-6); $^{13}$c-NMR (25.05 MHz, D$_2$O): 36.4 (C-2'); 42.3 (C-3'); 62.7, 63.6 (C-5', C-6'); 84.4, 88.2 (C-1', C-4'); 96.6 (C-5); 141.9 (C-6); 158.1 (C-2); 166.8 (C-4). β-Anomer: [α]$_D$$^{22}$: −76.3° (c 1.14 H$_2$O); UV (H$_2$O) λmax: 273 nm (ε 5333); $^1$H-NMR (270 MHz, D$_2$O): 2.2–2.46 (m, 3H, H-2; H-3'); 3.68 (d, J$_{3',6}$=5.5 Hz, 2H, H-6'); 3.76 (dd, J$_{4',5'a}$=5.5 Hz, J$_{5'a,5'b}$=12.5 Hz, 1H, H-5'a); 3.92 (dd, J$_{4',5'b}$=2.9 Hz, J$_{5'a,5'b}$=12.5 Hz, 1H, H-5'b); 4.01 (m, J$_{3',4}$=8.1 Hz, J$_{5a',4}$=5.5 Hz, J$_{5'b,4}$=2.9 Hz, 1H, H-4'); 6.05 (3, J$_{5,6}$=7.3 Hz, 1H, H-5); 6.11 (dd, J$_{1',2'a}$=7.0 Hz, J$_{1',2'b}$=4.0 Hz, 1H, H-1'); 7.91 (d, J$_{5,6}$=7.3 Hz, 1H, H-6); $^{13}$C-NMR (25.05 MHz, D$_2$O): 36.1 (C-2'); 40.8 (C-3'); 62.7, 63.1 (C-5', C-6'); 84.7, 87.1 (C-1', C-4'); 96.5 (C-5); 142.2 (C-6); 158.2 (C-2); 166.8 (C-4).

Example 7

9-[2',3'-Dideoxy-3'-C-(hydroxymethyl)-β-L-erythro-pentofuranosyl]-adenosine; and

Example 8

9-[2',3'-Dideoxy-3'-C-(hydroxymethyl)-α-L-erythro-pentofuranosyl]-adenosine

The α-anomer: [α]$_D$$^{22}$: −45.2° (c 0.37, H$_2$O); UV (H$_2$O) λ$_{max}$: 260 nm (ε 10987); $^1$H-NMR (270 MHz, D$_2$O): 2.45 (m, 1H, H-2'a); 2.6 (m, 1H, H-3') 2.92 (m, J$_{2'b,1}$=6 Hz, J$_{2'b,3}$=7.8 Hz, J$_{2'b,2'a}$=14 Hz, 1H, H-2'b); 3.72 and 3.74 (dd and d, overlapping, J$_{5'b,4}$=5.5 Hz, J$_{5'b,5'a}$=12.5 Hz, J$_{6',3}$=5.9 Hz, 3H, H-5'b and H-6'); 3.86 (q, J$_{5'a,4}$=2.9 Hz, J$_{5'a,5'b}$=12.5 Hz, 1H, H-5'a); 4.31 (m, 1H, H-4'); 6.35 (m, 1H, H-1'); 8.19 (s, 1H, H-2); 8.32 (s, 1H, H-8); $^{13}$C-NMR (25.05 MHz, D$_2$O): 35.5 (C-2'); 42.3 (C-3'); 62.5, 63.3 (C-5', C-6'); 83.8, 85.3 (C-1', C-4'); 119.4 (C-5); 140.3 (C-8); 148.9 (C-4); 153.0 (C-2); 155.9 (C-6). THe β-anomer: [a]$_D$$^{22}$ +22.5° (c 0.44, H$_2$O); UV (H$_2$O) λ$_{max}$: 260 nm (ε 11482); $^1$H-NMR (270 MHz, D$_2$O): 2.5 (m, 1H, H-3'); 2.67 (m, 2H, H-2'); 3.69 (dd, J$_{5'a,4}$=5.1 Hz, J$_{5'a,5'b}$=12.5 Hz, 1H, H-5'a); 3.77 (d, J$_{6',3}$=5.5 Hz, 2H, H-6'); 3.87 (dd, J$_{5'b,4}$=2.9 Hz, J$_{5'b,5'a}$=12.5 Hz, 1H, H-5'b); 4.13 (m, 1H, H-4'); 6.34 (m, 1H, H-1'); 8.18 (s, 1H, H-2); 8.32 (s, 1H, H-8). $^{13}$C-NMR (25.05 MHz D$_2$O); 35.7 (C-2'); 41.4 (C-3'); 62.8, 63.4 (C-5' and C-6'); 85.0, 85.3 (C-1' and C-4'); 119.2 (C-5); 140.5 (C-8); 148.7 (C-4); 153.0 (C-2); 155.8 (C-6).

Example 9

1-[2',3'-Dideoxy-3'-C-(hydroxymethyl)-β-L-erythro-pentofuranosyl]-thymine and

Example 10

1-[2',3'-Dideoxy-3'-C-(hydroxymethyl)-α-L-erythro-pentofuranosyl]-thymine

The α-anomer had $[\alpha]_D^{22}$: +8.3° (c 0.48, H$_2$O); UV (H$_2$O) $\lambda_{max}$: 268 nm (ε 7976); $^1$H-NMR (270 MHz, D$_2$O): 1.89 (d, J=1.1 Hz, 3H, 5-CH$_3$); 1.96 (mJ$_{2'a,2'b}$=13.2 Hz, J$_{2'a,3}$=9.9 Hz, J$_{2'a,1}$=7.7 Hz, 1H, H-2'a); 2.47 (m, 1H, H-3'); 2.6 (m, J$_{2'a,2'b}$=13.2 Hz, J$_{2'b,3}$=8.1 Hz, J$_{2'b,1}$=6.2 Hz, 1H H-2'b); 3.64, 3.68 (d and dd, overlapping, J$_{5',4'}$=5.5 Hz, J$_{5'a,5'b}$=12.1 Hz, J$_{6',3}$=6.1 Hz, 3H, H-6'a and H-6'); 3.81 (dd, J$_{5'b,5}$=2.9 Hz, J$_{5'b,5'a}$=12.1 Hz, H-5'b); 4.24 (m, J$_{3',4}$=8.4 Hz, J$_{4',5'a}$=5.5 Hz, J$_{4',5'b}$=2.9 Hz, 1H, H-4); 6.11 (dd, J$_{1',2'a}$=7.7 Hz, J$_{1,2'b}$= 6.2 Hz, 1H, H-1); 7.59 (d, J=1.1 Hz, 1H, H-6); $^{13}$c-NMR (25.05 MHz, D$_2$O): 12.5 (5-CH$_3$) 35.7 (C-2'); 42.7, (C-3') 62.6, 63.5 (C-5' and C-6'); 84.2, 87.3 (C-1' and C-4'); 111.6 (C-5); 138.1 (C-6); 152.4 (C-2); 167.3 (C-4).

The β-anomer: $[\alpha]_D^{22}$: −21.2° (c 0.32 H$_2$O); λ max: 268 nm (ε 8123); $^1$H-NMR (270 MHz, D$_2$O): 1.91 (s, 3H, 5-CH$_3$); 2.3 (m, 2H, H-2'); 2.5 (m,=1H, H-3'); 3.69 (d, J$_{3',6}$=5.9 Hz, 2H, H-6'); 3.76 (dd, J$_{5b,5'a}$=12.4 Hz, J$_{5'b,4}$=5.1 Hz, 1H, H-5'b); 3.9 (dd, J$_{5'a,5'b}$=12.4 Hz, J$_{5a',4}$=2.9 Hz, 1H, H$_{5'a}$); =3.99 (m, J$_{4',5'a}$=2.9 Hz, (J$_{4',5'b}$=5.1 Hz, J$_{4',3}$=8.1 Hz, 1H, H-4); 6.14 (dd, J$_{1',2'a}$=4.8 Hz, J$_{1',2'b}$=6.6 Hz, 1H, H-1); 7.73 (d, J=1.1 Hz 1H, H-6) $^{13}$C-NMR (25.05 MHz, D$_2$O): 12.5 (5-CH$_3$), 35.4 (C-2'); 40.9 (C-3'); 62.8, 62.9 (C-5' and C-6'); 84.5, 86.1 (C-1' and C-4'); 111.7 (C-5); 138.3 (C-6); 152.7 (C-2); 167.5 (C-4).

General procedure for the silylations used in Examples 11–16. A suspension consisting of the base (1 mmol) and a small crystal of ammonium sulfate in a mixture of hexamethyldisilazane (2 ml) and trimethylchlorosilane (0.2 ml) was refluxed until a clear solution was obtained. Volatile matters were evaporated off, and the residue was repeatedly coevaporated with added xylene.

Example 11

1-[2',3'-Dideoxy-3'-C-(fluoromethyl)-α- and β-D-erythro-pentofuranosyl]-thymine.

Thymine (150 mg, 1.19 mmol) was silylated according to the general procedure and dissolved in dichloromethane (5 ml) under nitrogen. To this solution was added methyl 5-O-benzoyl-3-C-(fluoromethyl)-2,3-dideoxy-D-erythro-pentofuranoside (200 mg, 0.75 mmol) followed by tert-butyldimethylsilyl triflate (0.3 ml, 1.31 mmol). The solution was stirred for 24 hours at room temperature, after which the reaction was quenched by the addition of aqueous sodium hydrogen carbonate, stirred for 30 min, diluted with dichloromethane, washed with aqueous sodium hydrogen carbonate, dried, and concentrated to give an anomeric mixture of the protected nucleosides. The mixture was treated with methanolic ammonia (20 ml, saturated) for 24 h at room temperature. After concentration to dryness, the residue was dissolved in water and washed with dichloromethane. The aqueous layer was concentrated to a small volume and the mixture was separated by column chromatography (ethyl acetate-methanol 20:1). The β-anomer was eluted first followed by the α-anomer. The appropriate fractions were combined and evaporated to give the title compounds, α (70 mg, 36%) and β (54 mg, 28%). α: $[\alpha]_D^{22}$−13.1° (c 0.82, H$_2$O); UV (H$_2$O) $\lambda_{max}$ 268 nm (ε 9268); $^1$H NMR (270 MHz, D$_2$O) δ 2.92 (5-CH$_3$), 2.06 (H-2'a), 2.60–2.82 (m, H-2'b and H-3'), 3.68 (dd, H-5'a), 3.85 (dd, H-5'b), 4.38 (m, H-4), 4.46–4.75 (2 m, H-6'a-b), 6.15 (t, H-1'), 7.60 (d, H-6). Anal. Calcd. for C$_{11}$H$_{15}$O$_4$N$_2$F: C, 51.16; H, 5.85; N, 10.85. Found: C, 50.91; H, 5.78; N, 10.85. β: $[\alpha]_D^{22}$+16.3° (c 0.6, H$_2$O); UV (H$_2$O) $\lambda_{max}$ 268 nm (ε 8880); $^1$H NMR (270 MHz, D$_2$O) δ 1.91 (d, 5-CH$_3$), 2.3 (m, H-2'), 2.73 (m, H-3'), 3.78 (dd, H-5'a), 3.94 (dd, J$_{4',5'b}$= 2.9 Hz, H-5'b), 4.1 (m, H-4), 4.44–4.73 (2 m, H-6'a,b), 6.15 (dd, H-1'), 7.77 (d, J=1.1 Hz, H-6). Anal. Calcd for C$_{11}$H$_{15}$O$_4$N$_2$F: c, 51.16; H, 5.85; N, 10.85. Found: C, 51.10; H, 5.76; N, 10.95.

Example 12

1-[2',3'-Dideoxy-3'-C-(fluoromethyl)-α-and-β-D-erythro-pentofuranosyl]cytosine.

Cytosine (200 mg, 1.8 mmol) was silylated according to the general procedure and the synthesis was proceded as described above to give the title compounds α (38 mg, 38%) and β (26 mg, 26%). α: $[\alpha]_D^{22}$−53.7° (c 0.94, H$_2$O); UV (H$_2$O) λhd max 272 nm (ε 7762); $^1$H NMR (270 MHz, D$_2$O) δ 1.98 (m, H-2'a), 2.58–2.80 (m, H-2'b and H-3'), 3.68 (H-5'a), 3.85 (dd, H-5'b), 4.37 (m, H-4), 4.39–4.72 (2 m, H-6'a,b), 6.04 (d, H-5), 6.12 (t, H-1'), 7.70 (d, H-6). Anal. Calcd. for C$_{10}$H$_{14}$O$_3$N$_3$F: C, 49.38; H, 5.80. Found: C; H. β $[\alpha]_D^{22}$+44.8° (c 0.6, H$_2$O); UV (H$_2$O) $\lambda_{max}$ 272 nm (ε 8515); $^1$H NMR (270 MHz, D$_2$O) δ 2.23 (m, H-2'a), 2.39 (m, J$_{2'b,3}$=8.5 Hz, H-2'b), 2.65 (m, H-3'), 3.77 (dd, H-5'a), 3.93 (dd, H-5'b), 4.11 (m, H-4), 4.43–4.73 (two m, H-6'a,b), 6.03 (d, H-5), 6.10 (dd, H-1'), 7.93 (d, H-6). Anal. Calcd. for C$_{10}$H$_{14}$O$_3$N$_3$F: C, 49.38; H, 5.80. Found: C; H.

Example 13

9-[2',3'-Dideoxy-3'-C-(fluoromethyl)-α-and-β-D-erythro-pentofuranosyl]adenine. 6-Chloropurine (120 mg, 0.78 mmol) was silylated according to the general procedure and the synthesis was proceeded as described above to give the title compounds α (25 mg, 26%) and β (37 mg, 39%). α: $[\alpha]_D^{22}$ 35.2° (c 0.71, H$_2$O); UV (H$_2$O) $\lambda_{max}$ 260 nm (ε 10239); $^1$H NMR (270 MHz, D$_2$O) δ 2.5 (m, H-2'a), 2.70–2.95 (m, H-2'b and H-3'), 3.73 (dd, H-5'a), 3.88 (dd, H-5'b), 4.40 (m, H-4), 4.52–4.78 (2 m, J$_{3',6'b}$=10.0 Hz, H-6'a-b), 6.34 (t, H-1'), 8.15 (s, H-2), 8.29 (s, H-8). Anal. Calcd. for C$_{11}$H$_{14}$O$_2$N$_5$F: C, 49.43; H, 5.28. Found: C; H. β: $[\alpha]_D^{22}$ −24.3° (c 0.9, H$_2$O); UV (H$_2$O) $\lambda_{max}$ 260 nm (ε 10364); $^1$H NMR (270 MHz, D$_2$O) δ 2.47–2.48 (2 m, H-2'a,b), 2.85 (m, H-3'), 3.69 (dd, H-5'a), 3.87 (dd, H-5'b), 4.21 (m, H-4), 4.51–4.78 (2 m, H-6'a,b), 6.24 (dd, H-1'), 8.04 (s, H-2), 8.25 (s, H-8). Anal. Calcd. for C$_{11}$H$_{14}$O$_2$N$_5$F: C, 49.43; H, 5.28. Found: C.; H..

Example 14

1-[2',3'-Dideoxy-3'-C-(azidomethyl)-α-and-β-D-erythro-pentofuranosyl]-thymine.

Thymine (133 mg, 1.06 mmol) was silylated according to the general procedure and dissolved in dichloromethane (5 ml) under nitrogen. To this solution was added methyl 3-C-(azidomethyl)-5-O-(benzoyl)-2',3'-dideoxy-D-erythro-pentofuranoside (154 mg, 0.53 mmol) followed by tert-butyldimethylsilyl triflate (0.25 ml, 1.09 mmol). The solution was stirred for 24 hours at room temperature, after which the reaction was quenched by the addition of aqueous sodium hydrogen carbonate, stirred for 30 min, diluted with dichloromethane, washed with aqueous sodium hydrogen carbonate, dried, and concentrated to give an anomeric mixture of the protected nucleosides. The mixture was treated with methanolic ammonia (20 ml, saturated) for 24 h at room temperature. After concentration to dryness, the residue was dissolved in water and washed with dichloromethane. The aqueous layer was concentrated to a small volume and freeze dried to give 110 mg (0.39 mmol, 74%) of an anomeric mixture of the deblocked nucleosides. The mixture was dissolved in a mixture of N,N-dimethylformamid and imidazole (53 mg, 0.78 mmol) followed by the addition of tert-butyldimethylsilyl chloride (70 mg, 0.46 mmol), and the solution was stirred for 3 h at room temperature. Water (1 ml) was added, and the mixture was stirred for 10 min, diluted with dichloromethane, washed with 1M hydrogen chloride, saturated aqueous hydrogen carbonate, dried, and concentrated. The anomers were separated by column chromatography (hexane-ethyl acetate 1:1), the α-anomer was eluted first followed by the β-anomer. Each of the anomers was separately treated with tetrabutylammonium fluoride (70 mg, 0.22 mmol) in tetrahydrofuran (2 ml) for 24 h, concentrated, the residue dissolved in water, and washed with dichloromethane. The aqueous layer was concentrated to a small volume and purified by HPLC (water-methanol, 80:20, v/v) to give the title compounds α (43 mg, 29%) and β (44 mg, 30%). α: $[\alpha]^{22}_D$ +3.1° (c 1.45, $H_2O$); UV ($H_2O$) $\lambda_{max}$ 268 nm (ε 9155); $^1$H NMR (270 MHz, $D_2O$) δ 1.92 (s, 5-$CH_3$), 2.02 (m, H-2'a), 2.50–2.74 (2 m, H-2'b and H-3'), 3.54 and 3.58 (2 dd, H-6'a,b), 3.67 (dd, H-5'a), 3.85 (dd, H-5'b), 4.25 (m, $J_{4',5'a}$=5.1 Hz, H-4), 6.12 (dd, H-1), 7.60 (d, H-6). Anal. Calcd. for $C_{11}H_{15}O_4N_2F$: C, 51.16; H, 5.85. Found: C.; H., β $[\alpha]^{22}_D$ 12.5° (c 0.96, $H_2O$); UV ($H_2O$) $\lambda_{max}$ 268 nm (ε 9434); $^1$H NMR (270 MHz, $D_2O$) δ 1.91 (s, 5-$CH_3$), 2.34 (dd, H-2'), 2.59 (m, H-3'), 3.47–3.61 (2 dd, H-6'a,b), 3.78 (dd, H-5'a), 3.94 (dd, H-5'b), 3.98 (m, H-4), 6.1 (t, H-1), 7.76 (s, 1H, H-6). Anal. Calcd. for $C_{11}H_{15}O_4N_5$: C, 46.97; H, 5.38. Found: C.; H..

Example 15

1-[2',3'-Dideoxy-3'-C-(azidomethyl)-α-and-β-D-erythro-pentofuranosyl]cytosine.

Cytosine (250 mg, 2.25 mmol) was silylated according to the general procedure and the synthesis was proceeded as above to give the title compounds α (84 mg, 43%) and β (45 mg, 23%) α: $[\alpha]^{22}_D$ –46.1° (c 1.15, $H_2O$); UV ($H_2O$) $\lambda_{max}$ 272 nm (ε 8320); $^1$H NMR (270 MHz, $D_2O$) δ 1.96 (m, H-2'a), 2.56 (m, H-3'), 2.74 (m, H-2'b), 3.46–3.58 (2 dd, H-6'a,b), 3.68 (dd, H-5'a), 3.85 (dd, H-5'b), 4.25 (m, H-5), 6.09 (t, H-1), 7.79 (d, H-6). Anal. Calcd. for $C_{10}H_{14}O_3N_6$: C, 45.10; H, 5.30; N, 31.57. Found: C, 44.87; H, 5.13; N, 31.37. β $[\alpha]^{22}_D$ 55.0° (c 0.99, H2O); UV ($H_2O$) $\lambda_{max}$ 272 nm (ε 8209); $^1$H NMR (270 MHz, $D_2O$) δ 2.22–2.58 (m, H-2' and H-3'), 3.48–3.61 (2 dd, H-6'), 3.79 (dd, H-5'a), 3.94 (dd, H-5'b), 4.0 (m, H-4'), 6.04 (d, H-5), 6.11 (dd, H-1'), 7.93 (d, H-6). Anal. Calcd. for $C_{10}H_{14}O_3N_6$: C, 45.10; H. 5.30. Found: C.; H..

Example 16

9-[2',3'-Dideoxy-3'-C-(azidomethyl)-α and β-D-erythro-pentofuranosyl]-adenine.

6-chloropurine (360 mg, 2.33 mmol) was silylated according to the general procedure and the synthesis was proceeded as above to give the title compounds α (38 mg, 17%) and β (39 mg, 17%). An analytical sample of each of the anomers was obtained by HPLC purification (water-methanol, 70:30, v/v). α: $[\alpha]^{22}_D$ +58.3° (c 1.0, $H_2O$); UV ($H_2O$) $\lambda_{max}$ 260 nm (ε 9353); $^1$H MNR 270 MHz, $D_2$, δ 2.43 (m, H-2'a), 2.67 (m, H-3'), 2.84 (m,H-2'b), 3.61 (d, H-6'), 3.73 (dd, H-5'a), 3.88 (dd,h-5'a), 4.28 (m, H-4'), 6.28 (t, H-1'), 8.11 (s, H-2), 8.28 (s, H-8). Anal. Calcd for $C_{11}H_{14}O_2N_8$: C, 45.51; Gm 4.86; N, 38.61. Found: C, 45.31; Gm 4.80; N, 38.30. β. $[\alpha]^{22}_D$ –27.6° (c 1.05, $H_2O$; UV ($H_2O$) $\lambda_{max}$ 260 nm (ε 14102); $^1$H NMR 270 MHz, $D_2O$) δ 2.52 (m, H-2'a), 2.75 (m, H-2'b, H-3'), 3.61 (dd, H-6'a), 3.64 (dd, $J_{3,6'b}$=6.2 Hz, H-6'b), 3.71 (dd, H-5'a, 3.88 (dd, H-5'b), 4.12 (m, H-4'), 6.36 (dd, and 3.0 Hz, H-1'), 8.19 (s, H-2), 8.33 (s, H-8). Anal. Calcd for $C_{11}H_{14}O_2N_8$: C, 45.51; H, 4.86; N, 38.61. Found: C, 45.28; H, 4.97; N, 38.36.

Example 17

9-[3S,4S)-3,4-di(hydroxymethyl)cyclopentyl]-guanosine

To a white suspension of $PPh_3$ (528 mg, 2.0 mmol) and 2-$NH_2$-6-Cl-purin (342 mg, 2.0 mmol in dry THF (14 ml) at room temperature under nitrogen, was added DEAD (Diethylazodicarboxylate) (0.33 ml, 2.3 mmol) and the yellowish suspension was stirred for an additional 4 h. 3,4-dibenzoyloxymethyl-cyclopentanol (20 mg, 0.57 mmol) in dry THF (5 ml) was added, and the mixture was stirred for an additional 30 min. The solvent was evaporated and the crude residue was purified by silica gel column chromatography (toluene-ethyl acetate, 1:1). The crude product was dissolved in MeOH (2 ml), aqeous NaOH(1M, 2 ml) was added dropwise, and the mixture was stirred at 80° C. for 4 h. After cooling, the reaction mixture was neutralized with aqeous HCl (2M), the aqeous phase was extracted several times with THF-Ethylacetate (1:1) and the solvents were evaporated. The crude product was purified by silica gel column chromatography (chloroform-methanol, 6:1). Recrystallisation from water afforded the title compound in a yield of 57 g (36%).

Example 18

1-(2',3'-Dideoxy-2'-C-hydroxymethyl-β-D-erythro-pentofuranosyl)-thymine

A mixture of thymine (253 mg, 2.01 mmol), chlorotrimethylsilane (0.300 ml) and some crystals of $(NH_4)_2SO_4$ in hexamethyldisilazane (4 ml) was refluxed under nitrogen for 6 h. The clear solution was concentrated and residual volatiles were co-evaporated with added toluene (5 ml). The residue was dissolved in a mixture of dichloromethane-acetonitrile (9:1, 10 ml) and a solution of 2-C-acetoxymethyl-1-O-acetyl-5-O-(tert-butyldiphenyl)silyl-D-erythro-pentofuranose (630 mg, 1.34 mmol) in the same solvent mixture as above (5 ml) was added. The solution was cooled on an ice bath and tert-butyldimethylsilyl triflate (0.370 ml, 1.16 mmol) was added dropwise. The mixture was stirred for 30 min on an ice bath followed by 15 h at room temperature. Pyridine (2 ml) was added and the mixture was filtered through a pad of silica gel. The filtrate was concentrated and the residue purified by column chromatography (toluene-acetone 1:1) to yield 1-(2'-C-acetoxymethyl-5'-O-tert-butyldiphenylsilyl-2',3'-dideoxy-β-D-erytro-pentofuranosyl)thymine. 100 mg, 0.186 mmol of this material was dissolved in 1M tetrabutylammonium fluoride×3 $H_2O$ in THF (9 ml) and stirred for 20 min at room temperature. The solution was concentrated and the residue purified by column chromatography (toluene-acetone 1:1). The product was dissolved in methanol (4 ml) and methanol saturated with ammonia (2 ml) was added. The solution was stirred over night, concentrated and the residue purified by column chromatography (chloroform-methanol 9:1) yielding the title compound (38 mg): $[\alpha]_D$ +9.1° (c 0.70, $H_2O$): $^{13}$C NMR ($D_2O$, 40° C.) 12.3 ($CH_3$, thymine), 29.2 (C-3'), 46.7 (C-2'), 62.4, 63.8 (C-5', C-6'), 81.0 (C-4'), 88.8 (C-1'), 112.2 (C-5, 138.6 (C-6), 152.5 (C-4), 167.2); $^1$H NMR ($D_2O$, 40° C.) 1.90 (s, 3H, $CH_3$, thymine), 2.09 (m, 2H, H-3', H-3"), 2.64 (m, 1H, H-2'), 3.76 (m, 4H, H-5', H-5", H-6', H-6"), 4.31 (m, H-4'), 5.93 (d, J=5.13 Hz, 1H, H-1'), 7.68 (s, 1H, H-6).

Anal. Calcd. for $C_{11}H_{16}O_5N_2$: C, 51.56; H, 6.29; N, 10.93. Found: C, 51.28; H, 6.11; N, 10.71.

Example 19

1-(2',3'-Dideoxy-2'-C-hydroxymethyl-β-D-erythro-pentofuranosyl)cytosine was synthesizied analogous to Example 12 using cytosine instead of thymine yielding (41 mg):[α]$_D$+31.2° (c 1.20, H$_2$O): $^{13}$C NMR (D$_2$O, 40° C.) 29.2 (C-3'), 47.6 (C-2'), 62.5, 64.0 (C-5', C-6'), 81.2 (C-4'), 89.8 (C-1'), 96.8 (C-5), 142.6 (C-6), 158.3 (C-4), 166.9 (C-2); $^1$H NMR (D$_2$O, 40° C.) 2.04 (m, 2H, H-3', H-3"), 2.55 (m, 1H, H-2'), 3.77 (m, 4H, H-5', H-5", H-6', H-6"), 4.33 (m, 1H, H-4'), 5.91 (d, J=4.77 Hz, 1H, H-1'), 6.05 (d, J=7.32 Hz, 1H, H-5), 7.85 (d, J=7.32 Hz, 1H, H-6).

Anal. Calcd. for C$_{10}$H$_{15}$O$_4$N$_3$×H$_2$O: C, 46.33; H, 6.61; N, 16.21. Found: C, 46.41; H, 6.31; N, 16.16.

Example 20

2',3'-Dideoxy-2'-C-hydroxymethyladenosine was synthesized analogous to Example 12 using adenine instead of thymine yielding (20 mg): [α]$_D$ −10.3° (c 0.20, H$_2$O): UV (H$_2$O) γ$_{max}$ 260 nm; $^{13}$C NMR (D$_2$O, 40° C.) 29.4 (C-3'), 46.8 (C-2'), 62.2, (C-5', C-6'), 81.4 (C-4'), 88.3 (C-1'), 141.2-169-4 (5 ArC); $^1$H NMR (D$_2$O, 40° C.) 2.21 (m, 2H, H-3', H-3"), 3.06 (m, 1H, H-2'), 3.76 (m, 4H, H-5", H-6', H-6"), 4.45 (m, 1H, H-4'), 6.07 (d, J=5.32 Hz, 1H, H-1'), 8.15, 8.30 (s, s, 2H, H-2, H-8).

Anal. Calcd. for C$_{11}$H$_{15}$O$_3$N$_5$: C, 49.81; H, 5.70; N, 26.40. Found: C, 50.01; H, 5.54; N, 26.35.

Example 21

1-(2'-C-Azidomethyl-2',3'-dideoxy-β-D-erytro-pentofuranosyl)-thymine.

A solution 1-(2'-C-acetoxymethyl-5'-O-tert-butyldiphenyl-2',4'-dideoxy-β-D-erytro-pentofuransyl)thymine (440 mg, 0.820 mmol) in methanol saturated with ammonia (15 ml) was stirred over night. The mixture was concentrated and the residue purified by column chromatography (toluene-acetone 1:1). The residue (170 mg, 344 mmol) was dissolved in pyridine (5 ml) and methanesulfonyl chloride (0.030 ml, 379 mmol) was added. After 1 h at room temperature, the solution was concentrated and the residue co-evaporated with added toluene. The residue was purified by column chromatogrphy (toluene-acetone 2:1) yielding 1-(5'-tert-butyldiphenylsilyl-2'-C-methanesulfonylmethyl-2',3'-dideoxy-β-D-erytro-pentofuranosyl)thymine which was dissolved in DMF (2 ml). Sodium azide (72 mg, 1.11 mmol) was added and the resulting suspension was stirred at 60° C. for 3 h. The mixture was concentrated and purified by column chromatography (toluene-acetone 2:1) (151 mg) (IR(CHCl$_3$) 2100 cm$^{-1}$), which was dissolved in 1M tetrabutylammonium fluoride×3 H$_2$O in THF (10 ml) at room temperature. After 10 min, the mixture was concentrated and the residue purified by column chromatography (toluene-acetone 1:1) yielding the title compound (72 mg), [α] D −31.3° (c 0.76, CHCl$_3$): IR (CHCl$^3$) 2100 cm-1 (azide): $^{13}$C NMR (CDCl$_3$) 12.5 (CH$_3$, thymine), 29.6 (C-3'), 44.5 (C-3), 52.0 (C-6'), 63.8 (C-5'), 79.8 (C-4'), 89.0 (C-1'), 111.0 (C-5), 136.6 (C-6), 150.9 (C-4) 164.4 (C-2); $^1$H NMR (CDCl$_3$) 1.89 (s, 3H, CH$_3$, thymine), 1.96 (m, 1H, H-3'), 2.28 (m, 1H, H-3"), 2.61 (m, 1H, H-2'), 3.53, 3.82 (m, m, 4H, H-5', H-5", H-6', H-6"), 4.29 (m, 1h, H-4') 5.81 (d, J=5.50 Hz, 1H, H1', 7.56 (s, 1H, H-6), 9.90 (s, 1H, H-3).

Anal. Calcd. for C$_{11}$H$_{15}$O$_4$N$_5$: C, 46.97; H, 5.38; N, 24.90. Found: C, 46.83; H, 5.21; N, 24.71.

Example 22

2'-C-Azidomethyl-2',3'-dideoxycytidine

A solution of 2'-C-acetoxymethyl-5'-O-tert-butyldiphenyl-2',3'-dideoxy-cytidine (260 mg, 0.489 mmol) in methanol saturated with ammonia (10 ml) was stirred over night at room temperature. The mixture was concentrated and the residue purified by column chromatography (chloroform-methanol 9:1) to give 395 mg of the de-o-acetylated cytidine analogue. To a stirred solution of this material (100 mg, 0.208 mmol) in pyridine (3 ml) was added methanesulfonyl chloride (0.020 ml, 0.250 mmol). After 1 h the solution was concentrated and the residue was coevaporated with added toluene. The residue was purified by column chromatography (chloroform-methanol 9:1) (110 mg) $^{13}$C NMR (CDCl$_3$) 37.3 (CH$_3$), 69.7 (C-6'); $^1$H NMR (CDCl$_3$) 3.08 (s, 3H, CH3), 4.50 (d, J=4.21 Hz, 2H, H-6', H-6"), 100 mg, 0.179 mmol of this compound was dissolved in DMF (2 ml) and sodium azide (41 mg, 0.628 mmol) was added. The resulting suspension was stirred at 60° C. for 3.5 h. The mixture was concentrated and the residue purified by column chromatography (toluene-acetone 2:1) (84 mg), (IR(CHCl$_3$) 2100 cm−1) this was dissolved in 1M tetrabutylammonium fluoride×3 H2O in THF (4 ml) at room temperature. After 15 min, the mixture was concentrated and the residue purified by column chromatography (chloroform-methanol 5:1) and then HPLC (reversed phase, methanol-water 85:15) yielding the title compound (36 mg): [α] D +54.4° (c 0.95, H$_2$O); IR(CHCl$_2$) 2100 cm$^{-1}$, (azide): $^{13}$C NMR (D$_2$O, 40° C.) 29.9 (C-3'), 44.9 (C-2'), 52.6 (C-6', 64.0 (C-5'), 80.8 (C-4'), 90.0 (C-1'), 97.1 C-5), 142.6 (C-6), 158.3 (C-4), 166.9 (C-2); $^1$H NMR (D$_2$O, 40° C.) 2.03 (m, 2H, H-3', H-3"), 2.61 (m, 1H, H-2'), 3.56 (m, 2H, H-6', H-6"), 3.75 (m, 2H, H-5', H-5"), 4.33 (m, 1H, H-4'), 5.92 (d, J=5.50 Hz, 1H, H-1'), 6.05 (d, J=7.32 Hz, 1H, H-5), 7.82 (d, J=7.32 Hz, 1H, H-6).

Anal. Calcd. for C$_{10}$H$_{14}$O$_3$N$_6$: 45.11; H, 5.30; N, 31.56. Found: C, 45.02; H, 5.41; N, 31.28.

Example 23

1-[5'-O-Benzoyl-3'-C-[(benzoyloxy)methyl]-2',3'-dideoxy-4'-thio-α-and-β-D-erythro-pentafuranosyl]thymine (18).

A suspension of thymine (150 mg, 1.19 mmol) and a small crystall of ammonium sulfate in a mixture of hexamethyldisilazane (2 ml) and trimethylchlorosilane (0.2 ml) was refluxed until a clean solution was obtained. Volatile matters were evaporated off and the residue was repeatedly co-evaporated with toluene. The resulting syrup was dissolved in dichloromethane (2 ml) under nitrogen. To this solution compound 16 (153 mg, 0.32 mmol) was added followed by the addition of tert.-butyldimethylsilyl triflate (0.075 mL, 0.33 mmol), mercuric acetate (0.102 g, 0.32 mmol). The solution was stirred for 24 h at room temperature. The reaction was quenched by the addition of saturated aqueous sodium hydrogen carbonate, dried, concentrated and purified by column chromatography (chloroform-ethyl acetate 1:1) to give (0.127 g, 87%). NMR indicated that coupling of thymine had occurred but the spectra were too complex to analyse without separating the anomers. This material was de-O-benzoylated using sodium in methanol at room temperature to give 1(3'-C-hydroxymethyl)-2',3'-dideoxy 4'-thio-α-and-β-D-erythro-pentofuranosyl) thymine.

Example 24

1-[5'-O-Benzoyl-3'-C-[(benzoyloxy)methyl]-2',3'-dideoxy-4'-thio-α-and-β-D-erythro-pentofuranosyl] cytosine. Cytosine (100 mg, 0.901 mmol) was silylated following the same procedure as for the preparation of 18 and dissolved in acetonitrile (3 ml) under nitrogen. Compound 17 (119 mg, 0.287 mmol) was added followed by the addition of tert.-butyldimethylsilyl triflate (0.13 ml, 0.574 mmol) and the solution was stirred for 1 h at 0° C. The reaction was quenched by the addition of saturated aqueous sodium hydrogen carbonate, stirred for 30 min, diluted with dichloromethane, washed with saturated aqueous sodium hydrogen carbonate, dried, concentrated and purified by column chromatography (ethyl acetate-methanol 4:1) to give an anomeric mixture of the protected nucleoside 19 (49 mg, 37%). NMR indicated that coupling of cytosine had occured but the spectra were too complex to analyse without separating the anomers. This material was de-O-benzoylated using sodium in methanol at room temperature to give 1(3'-C-hydroxymethyl)-2',3'-dideoxy 4'-thio-α-and-β-D-erythro-pentofuranosyl)cytosine.

Experimental

The starting materials for the compounds in Examples 1–4 were prepared by the following sequence of reactions a–d:

a) (2S,3R)-1-O-p-Bromobenzyl-3-C-(2'-propenyl)-1,2,4-butantriol (compound 2, Scheme 1). To a cold solution of allylmagnesium bromide −50° C. (20 ml, 1M) in 100 ml of dry diethyl ether under nitrogen atomosphere, a solution of (2S,3R)-3-[[(4-bromobenzyl)oxy]methyl]oxirane-2-methanol-1-(1.36 g, 5 mmol) in 140 ml of dry diethyl ether was added dropwise over 30 minutes. The mixture was vigorously stirred for 30 minutes at −50° C. and then quenched with saturated aqueous ammonium chloride. The organic phase was collected and the aqueous phase was extracted with diethyl ether. The organic phases were combined and washed with hydrogen chloride (1M), sodium hydrogen carbonate (sat.), dried, filtered, concentrated and separated by column chromatography (toluene: ethyl acetate, 1:5), to give 2 (1 g, 64%) [and 3 (0.4 g, 25%)], $[\alpha]^{22}_D$: +1.56 (c 1.03, CHCl$_3$); $^1$H-NMR (100 MHz, CDCl$_3$): 1.8 (m 1H, H-3); 2.13 (t, $J_{1',2}=J_{1',3}$=6.8 Hz, 2H, H-1'); 3.3 and 3.0 (broad, 2H, OH-2); 3.59 (m, 4H, H-1, H-4); 4.0 (m, 1H, H-2); 4.48 (s, 2H, CH$_2$Ph); 4.94 and 5.09 (m, 2H, H-3'a, H-3'b); 5.78 (m, 1H, H-2'); 7.14–7.5 (m, 4H, arom); $^{13}$C-NMR (25.05 MHz, CDCl$_3$): 30.6 (C-1'); 42.3 (C-3); 63.3 (C-4); 71.9, 72.3, 72.5 (CH$_2$Ph, C-1, C-2'); 116.4 (C-3'); 121.5, 129.1, 131.3 (aromatic C); 136.4 (C-2 and aromatic C);

b) (2S,3R)-4-O-Benzoyl-1-O-p-bromobenzyl-3-C-(2'-propenyl)-1,2,4-butan-triol (compound 4, scheme 1). Benzoyl chloride (3.21 ml, 27.6 mmol) was added dropwise to a solution of compound 2 (8.54 g, 27 mmol) in dry pyridine (50 ml) at 0° C. The reaction mixture was stirred at 0° C. for 15 minutes. Water (5 ml) was added and the solvent was evaporated. The residue was dissolved in dichloromethane and washed with hydrochloric acid (1M), aqueous sod-am hydrogen carbonate (sat.), dried, concentrated and purified by flash chromatography (toluene: ethyl acetate, 2:1) to give compound 4 (9.77 g, 86%). [α]22$_D$: +8.5 (c 0.71, CHCl$_3$); $^1$H-NMR (100 MHz, CDCl$_3$): 1.95–2.43 (m, 3H, H-3, H-1'); 2.59 (d, $J_{H(OH),2}$=3.9 Hz, 1H, OH-2); 3.54 (m, sec. order, 2H, H-1a, H-1b); 3.95 (m, 1H, H-2); 4.34 (d, $J_{4,3}$=5.1 Hz, 2H, H-4); 4.48 (s, 2H, CH$_2$Ph); 5.14 and 5.0 (m, 2H, H-3'a, H-3'b); 5.78 (m, 1H, H-2'); 8.1-7.14 (m, 9H, arom.); $^{13}$C-NMR (25.05 MHz, CDCl$_3$); 31.3 (C-1'; 40.4 (C-3); 70.1 C-2; 64.0 (C-4); 72.3 (CH$_2$Ph); 72.5 (C-1); 116.3 (C-3'); 121.4-134.7 (arom.); 136.4 (C-2'); 166.1 (COPh).

c) Methyl 3-C-[(benzoyloxy) methyl]-5-O-p-bromobenzyl-2,3-dideoxy-D-erythro-pentofuranoside (compound 5, scheme 1). To an ice cold mixture of compound 4 (7.5 g, 17.9 mmol) and N-methylmorpholine-N-oxide (4.8 g, 35.5 mmol) in tetrahydrofuran:water (3:1, 70 ml), OsO$_4$ in t-butanol (18 ml, 0.02M, stab. with 1% TBHP, 0.36 mmol) was added. After a few minutes, the ice bath was removed and the reaction mixture was stirred overnight at room temperature under nitrogen. NaHSO$_3$ (2 g) was added and the mixture was stirred for 15 minutes. The solvent was evaporated off and the residue diluted with ethyl acetate, washed with HCl (1M), NaHCO$_3$ (sat.), dried, filtered and concentrated. The crude product was dissolved in tetrahydrofuran:water (3:1, 200 ml) and treated with NaIO$_4$ (7.65 g, 35.8 mmol). The cis diol was completely cleaved after 30 minutes at room temperature. The tetrahydrofuran was evaporated off and the aqueous residue was saturated with NaCl, and extracted with diethyl ether. The organic phase was dried and concentrated. The residue was treated with methanolic HCl (0.05%, 50 ml) for ten minutes, neutralized with Dowex 2×8 (HCO$_3$), filtered, evaporated and the residue was purified by flash chromatography (toluene-ethyl acetate, 3:1) to give an anomeric mixture of compound 5 (6.63 g, 85%) as a colourless syrup. $^1$H-NMR (100 MHz, CDCl$_3$): 1.7–2.9 (three m, 3H, H-3, H-2a, H-2b); 3.31, 3.35 (2s, 3H, OCH$_3$); 3.6 (m, 2H, H-5); 4.1 (m, 1H, H-4); 4.4 (m, 2H, H-6); 4.6 (m, 2H, CH$_2$Ph); 5.1 (m, 1H, H-1); 7.1–8.0 (m, 9H, aromatic); $^{13}$C- NMR (25.05 MHz, CDCl$_3$): 35.6, 36.4 (C-2); 38.7, 39.3 (C-3); 54.3, 54.5 (OCH$_3$); 65.7, 66.6, (C-6); 71.5, 72.35, 72.37, 73.8 (C-5) (CH$_2$Ph); 79.9, 80.1 (C-4); 104.8 (C-1); 121.0–136.4 (aromatic); 165.8 ( COPh).

d) Methyl 5-O-benzoyl-3-C-[(benzoyloxy)methyl]-2,3,-dideoxy-D-erythro-pentafuranoside (compound 6, scheme 1). A solution of compound 5 (1 g, 2.3 mmol) in dry diethyl ether (3 ml) was dissolved in liquid ammonia (50 ml) in a dewar bottle. Sodium (300 mg, 13 mmol) was added in portions over 5 minutes. The solution was stirred for 30 minutes and then quenched with solid NH$_4$Cl. The ammonia was evaporated under a stream of nitrogen and the solid residue was diluted with ethyl acetate. The solid was filtered off and washed several times with ethyl acetate. The filtrate was concentrated and then co-evaporated with dry toluene. The crude residue was dissolved in dry pyridine (30 ml). Benzoylchloride (0.8 ml, 6.9 mmol) was added and the solution was stirred for 40 minutes at room temperature after which water (5 ml) was added and the mixture was concentrated to dryness. The residue was dissolved in CH$_2$Cl$_2$ and washed with aqueous HCl (1M), aqueous NaHCO$_3$ (sat.), dried, filtered and evaporated to dryness. Flash chromatography (toluene ethyal acetate, 3:1) yielded compound 6 (580 mg, 68%), as an anomeric mixture. A small sample of compound 6 was separated by silica gel. $^1$H-NMR and m.p. of the β-anomer were in agreement with those previously reported.

The starting materials for the compounds in Examples 11–16 were prepared by the following sequence of reactions a–e:

a) Methyl 5-O-(p-bromobenzyl)-3-C-(hydroxymethyl)-2, 3-dideoxy-D-erythro-pentofuranoside. Methyl 3-C-[(benzoyloxy]-5-O-(α-bromobenzyl)-2,3-dideoxy-D-erythro-pentofuranoside (1.61 mg, 3.70 mmol) was treated with methanolic ammonia (30 ml, saturated) for 24 h. The solvent was evaporated, and the residue was purified by flash column chromatography (toluene-ethyl acetate, 1:2) to give the title compound (1.14 g, 93%). Anal. Calcd for C$_{14}$H$_{19}$O$_4$Br: 50.77; H, 5.78. Found: C, 50.67; H, 5.73.

b) Methyl 5-O-(p-bromobenzyl)-3-C-(fluoromethyl)-2,4-dideoxy-D-erythro-pentofuransde. To a cold solution (−15° C.) of the previous compound (637 mg, 1.92 mmol) in dichloromethane (15 ml) and pyridine (0.31 ml, 3.85 mmol) under nitrogen, a solution of trifluoromethanesulfonic anhydride (0.38 ml, 2.26 mmol) in dichloromethane (5 ml) was added dropwise. After stirring for 10 min at −15° C., the mixture was diluted with dichloromethane (100 ml), washed with 1M hydrogen chloride, saturated aqueous sodium hydrogen carbonate, dried, and concentrated at a bath temperature not exceeding 20° C. The residue was treated with a solution of anhydrous tetrabutylammonium fluoride in tetrahydrofuran (6 ml, 1M) for 15 min. The mixture was concentrated and the residue was subjected to flash column chromatography (toluene-ethyl acetate, 9:1) to give the title compound (466 mg, 73%). Anal. Calcd for $C_{14}H18O_3BrF$: 50.46; H, 5.45. Found: C, 50.28; H.35.

c) Methyl 5-p-benzoyl-3-C-(fluoromethyl)-2,3-dideoxy-D-erythro-pentofuranoside. A mixture of the previous compound (572 mg, 1.72 mmol) in ethanol (40 ml) containing sodium hydrogen carbonate (excess) and 10% Pd on charcoal (50 mg) was treated with hydrogen for 5 h at ambient pressure. The solids were filtered off and the filtrate was concentrated. The crude residue was dissolved in a mixture of dichloromethane (3 ml) and pyridine (0.3 ml, 3.7 mmol), followed by the addition of benzoyl chloride (0.24 ml, 2.07 mmol). The reaction mixture was stirred for 15 min. Water (2 ml) was added, and the mixture was stirred for 10 min, diluted with dichloromethane, washed with 1M hydrogen chloride, saturated aqueous hydrogen carbonate, dried, and concentrated. The residue was purified by flash column chromatography (toluene-ethyl acetate, 4:1) to give the title compound (372 mg, 81%). Anal. Calcd. for $C_{14}H_{17}O_4F$: C, 62.68; H, 6.33. Found: C, 62.55; H, 6.33.

d) Methyl 3-C-(azidomethyl)-5-O-(p-bromobenzyl)-2,3-dideoxy-D-erythro-pentofuranoside.

To a mixture of methyl 5-O-(p-bromobenzyl-3-C-(hydroxymethyl)-2',3'-dideoxy-D-erythro-pentofuranoside (1.95 g, 5.89 mmol), triphenylphosphine (1.6 g, 6.1 mmol), and lithium azide (1.5 g, 30.6 mmol) in dry N,N-dimethylformamide (25 ml) was added carbon tetrabromide (1.95 g, 5.89 mmol) at room temperature. The mixture was vigorously stirred for 24 h. Methanol (3 ml) was added, and the solvent was evaporated. The mixture was diluted with dichloromethane, washed with water, dried, and concentrated. The residue was purified by flash column chromatography (toluene-ethyl acetate, 4:1) to give the title compound (1.99 g, 95%) $\gamma_{max}$ 2100 cm−1. Anal. Calcd. for $C_{14}H_{18}O_3BrN_3$: C, 47.20; H, 5.09; N, 11.80. Found:C, 47.15; H, 4.98; N, 11.9.

e) Methyl 3-C-(azidomethyl)-5-O-(benzoyl)-2,3-dideoxy-D-erythro-pentofuranoside. To a stirred solution of dry pyridine (4.7 ml, 58.3 mmol) and dichloromethane (20 ml) was added chromium trioxide (2.8 g, 28.0 mmol). The mixture was stirred for 15 min at room temperature. A solution of the previous compound (1.68 g, 4.72 mmol) in dichloromethane (20 ml) was added, followed by acetic anhydride (3.2 ml, 32.0 mmol), and the mixture was stirred for 10 min at room temperature. The mixture was passed through a short column of silica gel with ethyl acetate as eluent, to give a crude product, which was treated with methanolic ammonia (30 ml, saturated) for 24 h. The solvent was evaporated, and the residue was purified by flash column chromatography (toluene-ethyl acetate, 1:1) and then dissolved in a mixture of dichloromethane (15 ml) and pyridine (1 ml, 12.4 mmol), after which benzoyl chloride (0.55 ml, 4.73 mmol) was added. The reaction mixture was stirred for 15 min. Water (2 ml) was added, and the mixture was stirred for 10 min, diluted with dichloromethane, washed with 1M hydrogen chloride, saturated aqueous hydrogen carbonate, dried, and concentrated. The residue was purified by flash column chromatography (toluene-ethyl acetate, 9:1) to give the title compound (1.0 g 57%). Anal. Calcd for $C_{14}H_{17}O_4N_3$: C, 57.72; H, 5.88; N, 14.43. Found: C, 57.86; H, 5.74; N, 14.43.

The starting material for the compounds in Example 17 were prepared by the following sequence of reactions a–b:

a) (3S,4S)-3,4-di(benzoyloxymethyl)cyclopentanone (compound 8, Scheme 2). A mixture of (−)(3S,4S)-3,4-di(methoxycarbonyl)cyclopentanone (compound 7, Scheme 2) (0.93 g, 4.6 mmol), ethylene glycol (6.5 ml, 0.12 mol) and p-toluenesulfonic acid monohydrate (25 mg) in toluene (50 ml) was refluxed for 6 h with a Dean-Stark trap. Sodium hydrogen carbonate (20 mg) was added and after stirring for 5 min the mixture was washed with saturated aqueous sodium hydrogen carbonate, dried (MgSO$_4$) and concentrated to a crude ketal diester. According to 1H NMR, the product was free from unreacted ketone. The crude ketal diester in dry diethyl ether (15 ml) was added dropwise for 1 h to an ice-cold mixture of lithium aluminium hydride (0.35 g, 9.2 mmol) in dry diethyl ether (35 ml). The mixture was stirred at room temperature for 3 h before the excess of lithium aluminium hydride was decomposed by successive addition of water (0.5 ml), 3M aqueous NaOH (0.5 ml) and water (1.5 ml). After stirring for 1 h MgSO$_4$ (20 g) was added and the stirring was prolonged for 5 min. The precipitate and MgSO$_4$ were removed by filtration and washed several times with ethyl acetate. The filtrate was concentrated to give a crude oil of the diol. To a stirred solution of the diol in pyridine (13.5 ml) was added benzoyl chloride (2.3 ml, 20.1 mmol) dropwise. The mixture was stirred for 3 h in room temperature. Water (5 ml) was added and after stirring for 10 min, the mixture was diluted with saturated aqueous sodium hydrogen carbonate and dichloromethane. The organic layer was separated and washed with saturated sodium hydrogen carbonate, dried (MgSO$_4$) and concentrated. Column chromatography (toluene-EtOAc, 3:1) on a short column of silica gel gave a syrupy residue including the dibenzoylated ketal and traces of the dibenzoylated ketone. The syrup was dissolved in methanol (92 ml) and 2M aqueous HCl (31 ml), stirred at room temperature for 2 h and then at 50° C. for additional 2 h. The solution was neutralized with sodium hydrogen carbonate (5.2 g), diluted with water, extracted with dichloromethane. The organic layer was dried (MgSO$_4$), concentrated and crystallized from diethyl ether/hexane to give the title compound as needles (0.90 g, 55%): m.p. 85°–86° C.; $[\alpha]_D$−59.1° (c 1.04, chloroform); $^1$H NMR (100 MHz, CDCl$_3$) δ 2.12–2.73 (m, 6H, 2 CH, 2 CH$_2$), 4.50 (d, 4H, 2 CH$_2$-OBz), 7.36–7.64 and 7.94–8.07 (m, 10H, aromatic H); $^{13}$C NMR (25.05 MHz, CDCl$_3$) δ 38.3 (2 CH$_2$), 41.6 (2 CH) 65.9 (2 CH$_2$-OBz), 128.2, 128.2 and 133.0 (aromatic C), 165.9 and 214.9 (C=O). Anal. Calcd for $C_{21}H_{20}O_5$ (352.4): C, 71.58; H, 5.72. Found: C, 71.34; H, 5.73.

b) (3S,4S)-3,4-di(benzoyloxymethyl)cyclopentanol (compound 9, Scheme 2). To the compound 8 obtained under a) (193 mg, 0.55 mmol) in methanol (10 ml) was added sodium borohydride (41 mg, 1,10 mmol) in successive portions. The mixture was stirred at room temperature for 30 min, and then diluted with water and diethyl ether. The organic layer was washed with saturated aqueous sodium chloride, dried (MgSO$_4$) and concentrated to a syrup which was purified by column chromatography on silica gel (toluen/EtOAc, 1:1) to yield title compound (189 mg, 97%; $[\alpha]_D$−16.4° (c 1.09, chloroform); $^1$H NMR (100 MHz, CDCl$_3$) δ 1.6–2.7 (m, 7H, 2 CH, 2 CH$_2$, OH), 4.41 (t, 4H, 2 CH$_2$-OBz), 7.34–7.56 and 7.97–8.09 (m, 10H, aromatic H); $^{13}$C NMR (25.05 MHz, CDCl$_3$) δ 38.3, 39.3, 39.8, 40.0 (2 CH$_2$ 2 CH), 67.4, 68.2 (2 CH$_2$-OBz), 72.5 (CHOH), 128.1, 129.3, 129.8, 132.8 (aromatic C), 166.3 (C=O). Anal. Calcd for C$_{21}$H$_{22}$O$_5$ (354.4): C, 71.17; H, 6.26. Found: C, 71.05; H, 6.18.

The starting materials for the compounds in Examples 18–22 were prepared by the following sequence of reactions a–c:

a) (S)-4-tert-Butyldiphenylsilyloxy)methyl-(R,S)-2-hydroxymethyl-γ-butyrolactone (11). Ethanol (28 μl, 0.48 mmol) was added to sodium (280 mg, 12.17 mmol) in dry diethyl ether (5 ml), and the mixture was stirred at room temperature for 2 h. A solution of (S)-4-(tert-butyldiphenylsilyloxy)methyl-γ-butyrolactone (3.50 g, 9.87 mmol) and ethyl formate (980 mg, 13.23 mmol) in diethyl ether (6 ml) was added and the stirring was continued for 16 h at room temperature. Diethyl ether (20 ml) and 1M NaH$_2$PO$_4$ (10 ml) were added and the phases were separated. The organic phase was washed with water, dried and concentrated. The residue was dissolved in ethanol (10 ml), and a solution of NaBH$_4$ (500 mg, 13.22 mmol) in ethanol (10 ml) was added. After 5 min, the reaction was terminated by the addition of a few drops of 80% acetic acid. The mixture was partitioned between ethyl acetate and water. The organic phase was dried, concentrated and the residue purified by column chromatography (toluene-acetone 9:1) yielding 11 (3.40 g, 90%).

Anal. Calcd for C$_{22}$H$_{28}$O$_4$Si: C, 68.71; H, 7.34. Found: C, 68.58; H, 7.36.

b) (S)-2-Acetoxymethyl-(S)-4-(tert-butyldiphenylsilyloxy)methyl-γ-butyrolactone(12). A solution of 11 (2.00 g, 5.20 mmol) in pyridine (20 ml) and acetic anhydride (10 ml) was stirred at 60° C. for 30 min. The solution was concentrated and the residue purified by column chromatography (toluene-acetone 10:1) to give 12 (1.41 g, 64%): [α]$_D$ +22.4° (c 1.00, CHCl$_3$): $^{13}$C NMR (CDCl$_3$) δ 29.3 (C, tert), 20.8 (CH$_3$, acetate), 26.9 (3×CH$_3$), 27.3 (C-3), 39.8 (C-2), 63.1, 65.7 (CH$_2$OAc, C-5), 78.1 (C-4), 127.9, 128.3–135.7 (ArC), 170.7 (acetate), 176.4 (carbonyl); $^1$H NMR (CDCl$_3$) δ 1.05 (s, 9H, 3×CH$_3$), 2.07 (s, 3H, CH$_3$, acetate), 2.39 (m, 2H, H-3, H-3'), 3.13 (m, 1H, H-2), 3.79, 4.35 (m, m, 4H, H-5, H-5', H-6, H-6'), 4.58 (m, 1H, H-4), 7.17–7.72 (m, 10H, ArH).

Anal. Calcd. for C$_{24}$H$_{30}$O$_5$Si: C, 67.57; H, 7.09. Found: C, 67.48; H, 7.15.

c) 2-C-Acetoxymethyl-1-O-acetyl-5-O-(tert-butyldiphenyl)-silyl-D-erythro-pentofuranose (13). To a solution of lactone 12 (500 mg, 1.17 mmol) in toluene (30 ml) at −78° C. was added diisobutylaluminium hydride (20% in hexane, 3.00 ml, 2.95 mmol). The solution was stirred for 1.5 h, allowed to warm to room temperature, and methanol (0.5 ml) was added. To the solution was added ethyl acetate (30 ml) and aqueous sat. NaHCO$_3$ (4 ml). After stirring for 2 h, dry MgSO$_4$ (2.50 g) was added and after additional stirring for 3 h, the mixture was filtered. The filtrate was concentrated, the residue dissolved in pyridine (6 ml) and acetic anhydride (3 ml) and heated to 40° C. for 30 min, concentrated and the residue purified by column chromatography (toluene-acetone 10:1) to yield the title compound (500 mg, 91%) as an anomeric mixture. $^{13}$C NMR (CDCl$_3$, selected signals) δ 19.4 (C, tert.), 20.9, 21.3, 21.4 (CH$_3$, acetates), 26.9 (3×CH$_3$), 28.4 (C-3), 42.3, 44.8 (C-2), 62.8, 63.7, 65.8, 66.8 (C-5 and C-6), 80.0, 81.4 (C-4), 97.6, 100.2 (C-1), 127.8–135.7 (ArC), 170.2, 170.9 (acetates).

Anal. Calcd. for C$_{26}$H$_{34}$O$_6$Si: C, 66.35; H, 7.29. Found: C, 66.51; H, 7.28.

The starting materials for the compounds in Examples 23–24 were prepared by the following sequence of reactions a–c:

a) 5-O-Benzoyl-3-C-[(benzoyloxy)methyl]2,3-dideoxy-L-threo-pentose dibenzyl dithioacetal (15).

Compound 14 (0.191 g, 0.516 mmol) was treated at room temperature with benzyl mercaptane (0.24 ml, 2.07 mmol) in dichloromethane (3 ml) containing a catalytic amount of stannic chloride for 24 hours. The mixture was then diluted with dichloromethane and washed with saturated aqueous sodium hydrogen sulfate, dried, filtered, concentrated and purified by flash column chromatography (toluene-ethyl acetate 9:1) to give compound 15 (0.266 g, 88%) as a colourless syrup: [α]$^{22}_D$ −8.1° (c 1.0, CHCl$_3$). $^{13}$C NMR (25.05 MHz, CDCl$_3$) δ 34.0, 34.6, 34.9 (C-2, CH$_2$Ph), 38.9 (C-3), 47.9 (C-1), 63.2 (C-4), 67.6 (C-5), 69.8 (C-6), 127.1–138.0 (aromatic), 166.7 (COPh).

b) Benzyl 5-O-benzoyl-3-C-[(benzoyloxy)methyl]-2,3-dideoxy-1,4-dithio-α-and-β-D-erythro-pentofuranoside (16). To a solution of compound 15 (0.347 g, 0.592 mmol) in toluene-acetonitrile (2:1, 9 ml) were added triphenylphosphine (0.93 g, 3.55 mmol) and triiodoimidazole (0.79 g, 1.78 mmol). The mixture was kept at 100° C. over night. The mixture was diluted with toluene and washed with saturated aqueous sodium hydrogen sulfate, dried, filtered, concentrated and purified by column chromatography (toluene-ethyl acetate 50:1) to give 16 (0.219 g, 77%) as a colourless syrup: [α]$^{22}_D$−4.2° (c 1.0, CHCl$_3$); $^1$H NMR (100 MHz, CDCl$_3$) δ 2.0–2.3 (m, 2H, H-2), 2.8 (m, 1H, H-3), 3.8 (m, 3H, CH$_2$Ph, H-4), 4.5 (m, 5H, H-1, H-5, H-6), 7.1–8.1 (m, 15H, aromatic).

c) Acetyl 5-O-benzoyl-3-C-[(benzoyloxy)methyl]-2,3-dideoxy-4-thio-α-and-β-D-erythro-pentofuranoside (17). Compound 16 (0.182 g, 0.381 mmol) and mercuric acetate (0.243 g, 0.761 mmol) in glacial acetic acid (5 ml) were stirred at room temperature for 30 min. The solvent was evaporated and co-evaporated with dry toluene. The residue was diluted with dichloromethane, filtered through celite and concentrated. Flash chromatography (toluene-ethyl acetate 9:1) gave compound 17 (0.156 g, 99%) as a colourless syrup: $^1$H NMR (100 MHz, CDCl$_3$) δ 2.03, 2.07 (2s, 3H, COOCH$_3$), 2.3 (2H, H-2), 3.0 (m, 1H, H-3), 3.8 (m, 1H, H-4), 4.4 (m, 4H, H-5, H-6), 6.2 (m, 1H, H-1), 7.0–7.9 (m, 10H, aromatic).

Biological Tests

Test I. Effect of compounds of the formula I on HIV in H9 cells

HIV infection of H9 Cells

H9 cells, 10$^5$ cells per well on a 24 well plate, suspended in 2 ml RPMI-medium containing 10% fetal calf serum, 100 mg/ml penicillin, 10 mg/ml streptomycin sulfate and 2 mg/ml polybrene are exposed to HIV (HTLV-IIIB) and different concentrations of the test compounds. The plates are incubated at 37° C. in 5% CO$_2$ for 6–7 days. The contents in each well is then homogenized with a pipette and transferred to a centrifuge tube. After centrifugation for 10 min at 1500 rpm the supernatant is removed and the cell pellet is analyzed by fixing in methanol on glass plates. Human HIV positive serum diluted 1:80 or 1:160 is added and incubated for 30 min at 37° C. The plate is then washed with phosphate-buffered saline (PBS) containing Ca$^{2+}$ and Mg$^{2+}$. Sheep antihuman conjugate (FITC) is added and after a new incubation the plate is again washed with PBS. Contrast staining is done with Evans blue and after drying the frequency of HIV antigen containing cells is determined in a microscope. The test result is shown in Table 1.

TABLE 1

Concentration (mM) for 50% inhibition ($IC_{50}$) of human immuno deficiency virus multiplication in cell culture

| Compound | $IC_{50}$ μM |
|---|---|
| 1-[2',3'-Dideoxy-3'-C-(hydroxymethyl)-β-D--erythro-pentafuranosyl]cytosine | 0.01 |
| 1-[2',3'-Dideoxy-3'-C-(hydroxymethyl)-α-D--erythro-pentafuranosyl]cytosine | 5 |
| 1-[2',3'-Dideoxy-3'-C-(hydroxymethyl)-β-D--erythro-pentafuranosyl]thymine | 5 |
| 1-[2',3'-Dideoxy-3'-C-(hydroxymethyl)-α-D--erythro-pentafuranosyl]thymine | 10 |
| 9-[2',3'-Dideoxy-3'-C-(hydroxymethyl)-α-D--erythro-pentafuranosyl]adenine | 10 |

Table 1 shows that the tested compounds are active inhibitors of HIV virus multiplication.

Test II. Cellular Toxicity

H9 cells, $2\times10^7$ cells per plate, are incubated in RPMI-1640 medium containing 10% fetal calf serum, 70 mg/l penicillin, 100 mg/l streptomycin and 10 mM hepes, in absence or presence of test compounds. The number of cells per plate is determined after 48 h. Cells incubated in the absence of test compounds then underwent two cell division cycles.

F5000 cells, which are human embryo cells, $1\times10^5$ cells per plate, are incubated in Eagle's minimal essential medium, supplemented with Earle's sals, non-essential amino acids, 10% fetal calf serum, 10 mM hepes, 70 mg/l penicillin and 100 mg/l streptomycin, in absence or presence of test compounds. The number of cells per plate is determined after 48 h. Cells incubated in the absence of test compounds underwent one cell division cycle. The results are given as % inhibition of cell multiplication and are given in Table 2.

TABLE 2

| Cellular toxicity on H9 cells | |
|---|---|
| Compound | % Inhibition (H9) |
| 1-[2',3'-Dideoxy-3'-(hydroxymethyl)-β-D--erythro-pentofuranosyl]cytosine (1 mM) | 50 |

Table 2 shows that the concentration at which the compound exhibit toxicity exceed the concentration needed for 50% inhibition of HIV multiplication as given in Table 1.

We claim:

1. A compound of the formula

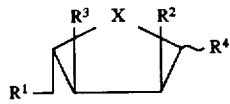

1B wherein X is O, S, SO, $SO_2$, $CH_2$; $R^1$ is OH, O—PO$(OH)_2$, O—PO(OH)—O—PO—$(OH)_2$, O—PO(OH) —O—PO(OH)—O—PO$(OH)_2$ or $(CH_2)_nOCH_2PO(OH)_2$ wherein n is 0–2;

$R^2$ is H and $R^3$ is $CH_3$, $CH_2OH$, $CH_2OCH_3$, $CH_2SH$, $CH_2F$ or $CH_2N_3$; or $R^3$ is H and $R^2$ is $CH_3$, $CH_2OH$, $CH_2OCH_3$, $CH_2SH$, $CH_2F$ or $CH_2N_3$;

$R^4$ is

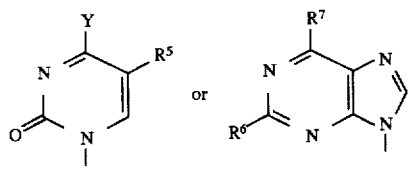

Y is OH, $NH_2$ and $R^5$ is $CH=CH_2$, $C\equiv CH$, $CH=CH—CH_3$, $C\equiv C—CH_3$, thien-2-yl, thien-3-yl, H, $CH_3$, $C_2H_5$, $CH_2CH_2CH_3$ or $CH(CH_3)_2$;

$R^6$ and $R^7$ are the same or different and are H, F, Cl, OH, $NH_2$ or SH;

in the form of a mixture of α- and β-anomers or in the form of an α- or β-anomer; and pharmaceutically acceptable salts thereof.

2. A compound according to claim 1 in the form of a β-anomer.

3. A compound according to claim 1 wherein X is O.

4. A compound according to claim 1 wherein X is S, SO or $SO_2$.

5. A compound according to claim 1 wherein X is $CH_2$.

6. A compound according to any of claims 1–5 wherein $R^1$ is OH; $R^2$ is H and $R^3$ is $CH_2OH$; $R^3$ is H and $R^2$ is $CH_2OH$.

7. A compound according to any of claims 1–5 wherein $R^1$ is OH; $R^2$ is H and $R^3$ is $CH_3$, $CH_2SH$, $CH_2OCH_3$, $CH_2F$, $CH_2N_3$; $R^3$ is H and $R^2$ is $CH_3$, $CH_2SH$, $CH_2OCH_3$, $CH_2F$, $CH_2N_3$.

8. A compound according to any of claims 1–5 wherein $R^1$ is $(CH_2)_nOCH_2PO(OH)_2$ and n is 0–2.

9. A compound according to any of claims 1–5 wherein X is OH, $NH_2$ and $R^5$ is H, $CH_3$, $CH=CH_2$, $C\equiv CH$ or $CH=CH—CH_3$.

10. A compound according to any of claims 1–5 wherein $R^6$ is $NH_2$ when $R^7$ is H, OH, SH or $NH_2$.

11. A compound according to any of claims 1–5 wherein $R^6$ is H, F or Cl when $R^7$ is OH, SH or $NH_2$.

12. A compound according to claim 1 wherein $R^6$ and $R^7$ are OH.

13. A compound according to claim 1 in the form of an α-anomer.

14. A pharmaceutical composition comprising as an active ingredient a compound of the formula 1B according to claim 1 and a pharmaceutically acceptable carrier, including liposomes.

* * * * *